United States Patent
Yukumoto et al.

(10) Patent No.: US 11,839,909 B2
(45) Date of Patent: Dec. 12, 2023

(54) WASTE TREATMENT SYSTEM AND WASTE TREATMENT METHOD

(71) Applicant: MITSUBISHI HEAVY INDUSTRIES, LTD., Tokyo (JP)

(72) Inventors: Atsuhiro Yukumoto, Tokyo (JP); Akira Noma, Tokyo (JP); Yoshio Seiki, Tokyo (JP); Yasumichi Aoki, Tokyo (JP); Nobuyuki Ukai, Tokyo (JP); Kazuhiro Kawai, Tokyo (JP); Jun Satou, Tokyo (JP); Susumu Okino, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 0 days.

(21) Appl. No.: 17/045,346

(22) PCT Filed: Apr. 11, 2019

(86) PCT No.: PCT/JP2019/015792
§ 371 (c)(1),
(2) Date: Oct. 5, 2020

(87) PCT Pub. No.: WO2019/198794
PCT Pub. Date: Oct. 17, 2019

(65) Prior Publication Data
US 2021/0146410 A1 May 20, 2021

(30) Foreign Application Priority Data
Apr. 13, 2018 (JP) .................................. 2018-077942

(51) Int. Cl.
*B09B 3/45* (2022.01)
*C02F 11/04* (2006.01)
(Continued)

(52) U.S. Cl.
CPC .................. *B09B 3/45* (2022.01); *B09B 3/40* (2022.01); *C02F 11/04* (2013.01); *C10L 5/42* (2013.01);
(Continued)

(58) Field of Classification Search
CPC ... B09B 3/45; B09B 3/40; C02F 11/04; C02F 11/12; C02F 11/18; C02F 2301/08;
(Continued)

(56) References Cited

U.S. PATENT DOCUMENTS

2011/0179981 A1 7/2011 Van Naarden et al.

FOREIGN PATENT DOCUMENTS

| EP | 2 518 024 | 10/2012 |
| JP | 4-313604 | 11/1992 |

(Continued)

OTHER PUBLICATIONS

Notice of Reasons for Refusal dated Mar. 15, 2022 corresponding Japanese Patent Application No. 2019-232716, with Machine Translation.
(Continued)

*Primary Examiner* — Latosha Hines
(74) *Attorney, Agent, or Firm* — Wenderoth, Lind & Ponack, L.L.P.

(57) ABSTRACT

A waste treatment system 100 for performing a hydrothermal treatment of wastes includes a hydrothermal treatment device 10 for performing the hydrothermal treatment by bringing steam into contact with the wastes, a storage facility 8, 9 for storing a fuel produced from a reactant of the hydrothermal treatment, and a heat recovery steam generator 18 for generating the steam to be supplied to the hydrothermal treatment device 10. The heat recovery steam generator
(Continued)

18 is configured to generate the steam by using a combustion energy generated by combustion of the fuel stored in the storage facility 8, 9.

23 Claims, 21 Drawing Sheets

(51) Int. Cl.
    *C10L 5/42*     (2006.01)
    *C10L 5/44*     (2006.01)
    *C10L 5/46*     (2006.01)
    *C12P 5/02*     (2006.01)
    *F01K 21/00*     (2006.01)
    *F22B 1/02*     (2006.01)
    *F22G 3/00*     (2006.01)
    *B09B 3/40*     (2022.01)
    *C02F 11/18*     (2006.01)
    *C02F 11/12*     (2019.01)

(52) U.S. Cl.
    CPC ............. *C10L 5/445* (2013.01); *C10L 5/46* (2013.01); *C12P 5/023* (2013.01); *F01K 21/00* (2013.01); *F22B 1/02* (2013.01); *F22G 3/00* (2013.01); *C02F 11/12* (2013.01); *C02F 11/18* (2013.01); *C10L 2200/0469* (2013.01); *C10L 2290/02* (2013.01); *C10L 2290/06* (2013.01)

(58) Field of Classification Search
    CPC .... C02F 2303/10; C02F 2303/24; C02F 9/00; C10L 5/42; C10L 5/445; C10L 5/46; C10L 2200/0469; C10L 2290/02; C10L 2290/06; C10L 2290/04; C10L 2290/08; C10L 2290/26; C10L 2290/54; C10L 3/08; C10L 9/086; C12P 5/023; F01K 21/00; F22B 1/02; F22G 3/00

See application file for complete search history.

(56) References Cited

FOREIGN PATENT DOCUMENTS

| | | | |
|---|---|---|---|
| JP | 2004-82094 | | 3/2004 |
| JP | 2004-89773 | | 3/2004 |
| JP | 2004089773 A | * | 3/2004 |
| JP | 2005-40671 | | 2/2005 |
| JP | 2005-139443 | | 6/2005 |
| JP | 2005-314549 | | 11/2005 |
| JP | 2008-173612 | | 7/2008 |
| JP | 2008221142 A | * | 9/2008 |
| JP | 2008-290041 | | 12/2008 |
| JP | 2010-106133 | | 5/2010 |
| JP | 2010-185021 | | 8/2010 |
| JP | 2010-195994 | | 9/2010 |
| JP | 2011-200836 | | 10/2011 |
| JP | 4937059 | | 5/2012 |
| JP | 2013-511386 | | 4/2013 |
| JP | 2015-96259 | | 5/2015 |

OTHER PUBLICATIONS

Notice of Reasons for Refusal dated Mar. 22, 2022 corresponding Japanese Patent Application No. 2019-232764, with Machine Translation.

International Search Report dated Jul. 16, 2019 in International (PCT) Application No. PCT/JP2019/015792, with English translation.

International Preliminary Report on Patentability and Written Opinion of the International Searching Authority dated Oct. 22, 2020 in International (PCT) Application No. PCT/JP2019/015792, with English translation.

Notice of Reasons for Refusal dated Feb. 5, 2019 in corresponding Japanese Patent Application No. 2018-077942, with Machine Translation.

Notice of Reasons for Refusal dated Jul. 2, 2019 in corresponding Japanese Patent Application No. 2018-077942, with Machine Translation.

* cited by examiner

WASTE TREATMENT SYSTEM AND WASTE TREATMENT METHOD

TECHNICAL FIELD

The present disclosure relates to a waste treatment system and a waste treatment method.

BACKGROUND

It is desired to effectively use unused biomass, for example, urban wastes discharged from a household, a food factory, and the like, agricultural wastes such as rice straw, wheat straw, and palm residue, livestock excreta, and sewage sludge. For example, in a technique described in Patent Document 1, wastes are hydrothermally treated, and a solid fuel (fuel) is produced from a solid phase of a reactant obtained by the hydrothermal treatment. Then, steam is generated by using a combustion energy generated by combustion of the solid fuel, and the above-described hydrothermal treatment is performed by using the generated steam.

CITATION LIST

Patent Literature

Patent Document 1: JP2013-511386A (see FIG. 2, in particular)

SUMMARY

Technical Problem

The amount of wastes varies according to collection conditions such as a collection period, a season, and a collection site. Thus, the amount of steam used for the hydrothermal treatment also varies according to the collection conditions. However, in the technique described in Patent Document 1 above, the fuel produced from the reactant of the hydrothermal treatment is combusted directly, and it is impossible to optionally change the steam amount. Thus, in the technique described in Patent Document 1, it is impossible to change the steam amount in accordance with the waste amount.

An object of at least one embodiment of the present invention is to provide a waste treatment system and a waste treatment method capable of changing a steam amount in accordance with a waste amount.

Solution to Problem (1) A waste treatment system according to at least one embodiment of the present invention is a waste treatment system for performing a hydrothermal treatment of wastes, the system including at least one hydrothermal treatment device for performing the hydrothermal treatment by bringing steam into contact with the wastes, a fuel production device for producing a solid fuel from solids of a reactant of the hydrothermal treatment, a methane fermentation device for performing methane fermentation of a liquid of the reactant to generate a biogas, a first storage facility for storing the fuel, a third storage facility for storing the biogas, and at least one steam generation device for generating the steam to be supplied to the hydrothermal treatment device. The steam generation device is configured to generate the steam by using the fuel stored in the first storage facility or a combustion energy generated by combustion of the biogas stored in the third storage facility, and the fuel production device includes a drying device for drying the solids of the reactant.

With the above configuration (1), it is possible to provide a waste treatment system capable of changing a steam amount in accordance with a waste amount, to produce a combustible solid fuel by drying the reactant of the hydrothermal treatment, and to store both of the solid fuel and the biogas generated from the reactant of the hydrothermal treatment.

(2) In some embodiments, in the above configuration (1), the waste treatment system includes a gasification furnace for gasifying the solid fuel to generate a fuel gas, and a second storage facility for storing the fuel gas generated in the gasification furnace.

With the above configuration (2), it is possible to store both of the solid fuel and the fuel gas generated from the solid fuel.

(3) A waste treatment system according to at least one embodiment of the present invention is a waste treatment system for performing a hydrothermal treatment of wastes, the system including at least one hydrothermal treatment device for performing the hydrothermal treatment by bringing steam into contact with the wastes, a methane fermentation device for performing methane fermentation of a liquid of the reactant to generate a biogas, a second hydrothermal treatment device for performing a hydrothermal treatment by bringing steam into contact with solids in a fermented matter obtained in the methane fermentation device, a first storage facility for storing a fuel produced from each of a reactant of the hydrothermal treatment and a second reactant of the hydrothermal treatment in the second hydrothermal treatment device, a third storage facility for storing the biogas, and at least one steam generation device for generating the steam to be supplied to the at least one hydrothermal treatment device. The steam generation device is configured to generate the steam by using the fuel stored in the first storage facility or a combustion energy generated by combustion of the biogas stored in the third storage facility.

With the above configuration (3), with the second hydrothermal treatment device, it is possible to perform a further hydrothermal treatment on the fermented matter. Thus, dehydration efficiency is improved by micronizing the fermented matter, and it is possible to easily separate the second treated object that has undergone the hydrothermal treatment in the second hydrothermal treatment device into solids and a liquid, and to easily produce the fuel.

(4) In some embodiments, in the above configuration (3), the second hydrothermal treatment device is configured to dry the second reactant obtained by the hydrothermal treatment in the second hydrothermal treatment device.

With the above configuration (4), the second hydrothermal treatment device itself that has performed the hydrothermal treatment can dry the second reactant obtained by the hydrothermal treatment.

(5) In some embodiments, in any one of the above configurations (1) to (4), the waste treatment system includes a power generation device for generating power by using the fuel or the combustion energy generated by combustion of the biogas.

With the above configuration (5), it is possible to generate power by using the fuel produced in the waste treatment system.

(6) In some embodiments, in the above configuration (5), the power generation device includes a steam turbine and a generator body part connected to the steam turbine, and the steam turbine is configured to be driven by at least a part of the steam generated in the steam generation device.

With the above configuration (6), the steam drives the steam turbine, and the generator body part connected to the steam turbine can generate power.

(7) In some embodiments, in the above configuration (5), the power generation device includes a gas engine and a generator body part connected to the gas engine, and the steam generation device is configured to generate steam by exhaust heat of the gas engine.

(8) In some embodiments, in the above configuration (6), the waste treatment system includes a combustion furnace for combusting the fuel, and a re-heater for superheating the steam by using a combustion energy generated in the combustion furnace.

With the above configuration (8), the steam drives the steam turbine, and the generator body part connected to the steam turbine can generate power.

(9) In some embodiments, in any one of the above configurations (5) to (8), the power generation device includes a first power generation device and a second power generation device.

With the above configuration (9), it is possible to optionally change the number of power generation devices used, in accordance with a power demand. Thus, it is possible to flexibly change the power generation amount in accordance with the power demand, and to stably supply power.

(10) In some embodiments, in any one of the above configurations (5) to (9), the waste treatment system includes a fluidized-bed furnace for combusting the fuel, and the steam generation device is configured to generate steam by using a combustion energy generated in the fluidized-bed furnace.

With the above configuration (10), with the fluidized-bed furnace, it is possible to combust the fuel rapidly while suppressing a variation in combustion. Thus, it is possible to generate steam rapidly while suppressing the variation in generation amount.

(11) In some embodiments, in any one of the above configurations (5) to (9), the waste treatment system includes a fluidized-bed furnace for combusting the fuel, and a feed-water heater for heating water to be supplied to the steam generation device, and the feed-water heater is configured to heat the water by using a combustion energy generated in the fluidized-bed furnace.

With the above configuration (11), with the fluidized-bed furnace, it is possible to combust the fuel rapidly while suppressing the variation in combustion. Thus, it is possible to generate steam rapidly while suppressing the variation in generation amount.

(12) A waste treatment system according to at least one embodiment of the present invention is a waste treatment system for performing a hydrothermal treatment of wastes, the system including at least one hydrothermal treatment device for performing the hydrothermal treatment by bringing steam into contact with the wastes, a third hydrothermal treatment device for obtaining a third reactant by a hydrothermal treatment of wastes containing at least one of a resin or an oil and a fat, a fuel production device for producing a solid fuel from each of the third reactant and a reactant of the hydrothermal treatment in the at least one hydrothermal treatment device, a first storage facility for storing the fuel, and at least one steam generation device for generating the steam to be supplied to the hydrothermal treatment device. The steam generation device is configured to generate the steam by using a combustion energy generated by combustion of the fuel stored in the first storage facility, the fuel production device includes a drying device for drying solids of the reactant and solids of the third reactant, and the fuel production device is configured to produce the solid fuel by using the third reactant.

With the above configuration (12), it is possible to produce the solid fuel by using the third wastes as a binder.

(13) A waste treatment system according to at least one embodiment of the present invention is a waste treatment system for performing a hydrothermal treatment of wastes, the system including at least one hydrothermal treatment device for performing the hydrothermal treatment by bringing steam into contact with the wastes, at least one storage facility for storing a fuel produced from a reactant of the hydrothermal treatment, and at least one steam generation device for generating the steam to be supplied to the hydrothermal treatment device. The steam generation device is configured to generate the steam by using a combustion energy generated by combustion of the fuel stored in the storage facility. The at least one hydrothermal treatment device includes a body part for performing the hydrothermal treatment, and a bucket for forming an interior space communicating with the body part via a reactant discharge port. The bucket is connected to a discharge pipe for discharging a gas existing in the interior space to an outside of the interior space.

With the above configuration (13), it is possible to suppress discharge of the gas (such as ammonia or the like) exhausted to the bucket to the atmosphere, when the reactant is extracted from the body part.

(14) In some embodiments, in any one of the above configurations (1) to (13), the at least one hydrothermal treatment device includes two hydrothermal treatment devices, and each of the two hydrothermal treatment devices has a steam supply port and a steam discharge port, and the steam discharge port of one of the two hydrothermal treatment devices and the steam supply port of the other of the two hydrothermal treatment devices are connected by a pipe.

With the above configuration (14), it is possible to use the steam that has used in one of the two hydrothermal treatment devices in the other hydrothermal treatment device. Thus, it is possible to reduce a usage of new steam.

(15) In some embodiments, in any one of the above configurations (1) to (14), the at least one hydrothermal treatment device includes a batch hydrothermal treatment device.

With the above configuration (15), for example, it is possible to load the wastes to the hydrothermal treatment device directly from a vehicle (not shown) for collecting the wastes, and to achieve pitless of the waste treatment system.

(16) A waste treatment system according to at least one embodiment of the present invention is a waste treatment method for performing a hydrothermal treatment of wastes, the method including a hydrothermal treatment step of performing the hydrothermal treatment by bringing steam into contact with the wastes, a fuel production step of producing a solid fuel from solids of a reactant of the hydrothermal treatment, a methane fermentation step of performing methane fermentation of a liquid of the reactant to generate a biogas, a step of storing the fuel, a step of storing the biogas, and a steam generation step of generating the steam to be used in the hydrothermal treatment step. The steam generation step includes generating the steam by using a combustion energy generated by combustion of the fuel stored in the storage step, and the fuel production step includes a drying step of drying the solids of the reactant. The fuel and the biogas are stored in different storage facilities.

With the above configuration (16), it is possible to provide a waste treatment method capable of changing a steam amount in accordance with a waste amount, to produce a combustible solid fuel by drying the reactant of the hydrothermal treatment, and to store both of the solid fuel and the biogas generated from the reactant of the hydrothermal treatment.

(17) A waste treatment system according to at least one embodiment of the present invention is a waste treatment method for performing a hydrothermal treatment of wastes, the method including a hydrothermal treatment step of performing the hydrothermal treatment by bringing steam into contact with the wastes, a methane fermentation step of performing methane fermentation of a liquid of a reactant of the hydrothermal treatment to generate a biogas, a second hydrothermal treatment step of performing a hydrothermal treatment by bringing steam into contact with solids in a fermented matter obtained in the methane fermentation device, a step of storing a fuel produced from a reactant of each of the hydrothermal treatments in the hydrothermal treatment step and the second hydrothermal treatment step, and a steam generation step of generating the steam to be used in the hydrothermal treatment step. The steam generation step includes generating the steam by using a combustion energy generated by combustion of the fuel stored in the storage step.

With the above configuration (17), with the second hydrothermal treatment step, it is possible to perform a further hydrothermal treatment on the fermented matter. Thus, dehydration efficiency is improved by micronizing the fermented matter, and it is possible to easily separate the second treated object that has undergone the hydrothermal treatment in the second hydrothermal treatment step into solids and a liquid, and to easily produce the fuel.

(18) A waste treatment system according to at least one embodiment of the present invention is a waste treatment method for performing a hydrothermal treatment of wastes, the method including a hydrothermal treatment step of performing the hydrothermal treatment by bringing steam into contact with the wastes, a third hydrothermal treatment step of obtaining a third reactant by a hydrothermal treatment of wastes containing at least one of a resin or an oil and a fat, a fuel production step of producing a solid fuel from each of the third reactant and a reactant of the hydrothermal treatment, a storage step of storing the fuel produced from the reactant of the hydrothermal treatment, a steam generation step of generating the steam to be used in the hydrothermal treatment step, and a fuel production step of producing a solid fuel from each of solids of the reactant and solids of the third reactant. The steam generation step includes generating the steam by using a combustion energy generated by combustion of the fuel stored in the storage step, and the fuel production step includes a drying step of drying the solids of the reactant and the solids of the third reactant.

With the above configuration (18), it is possible to produce the solid fuel by using the third wastes as the binder.

Advantageous Effects

According to at least one embodiment of the present invention, it is possible to provide a waste treatment system and a waste treatment method capable of changing the amount of water vapor in accordance with a waste amount.

DETAILED DESCRIPTION

Figure 1:
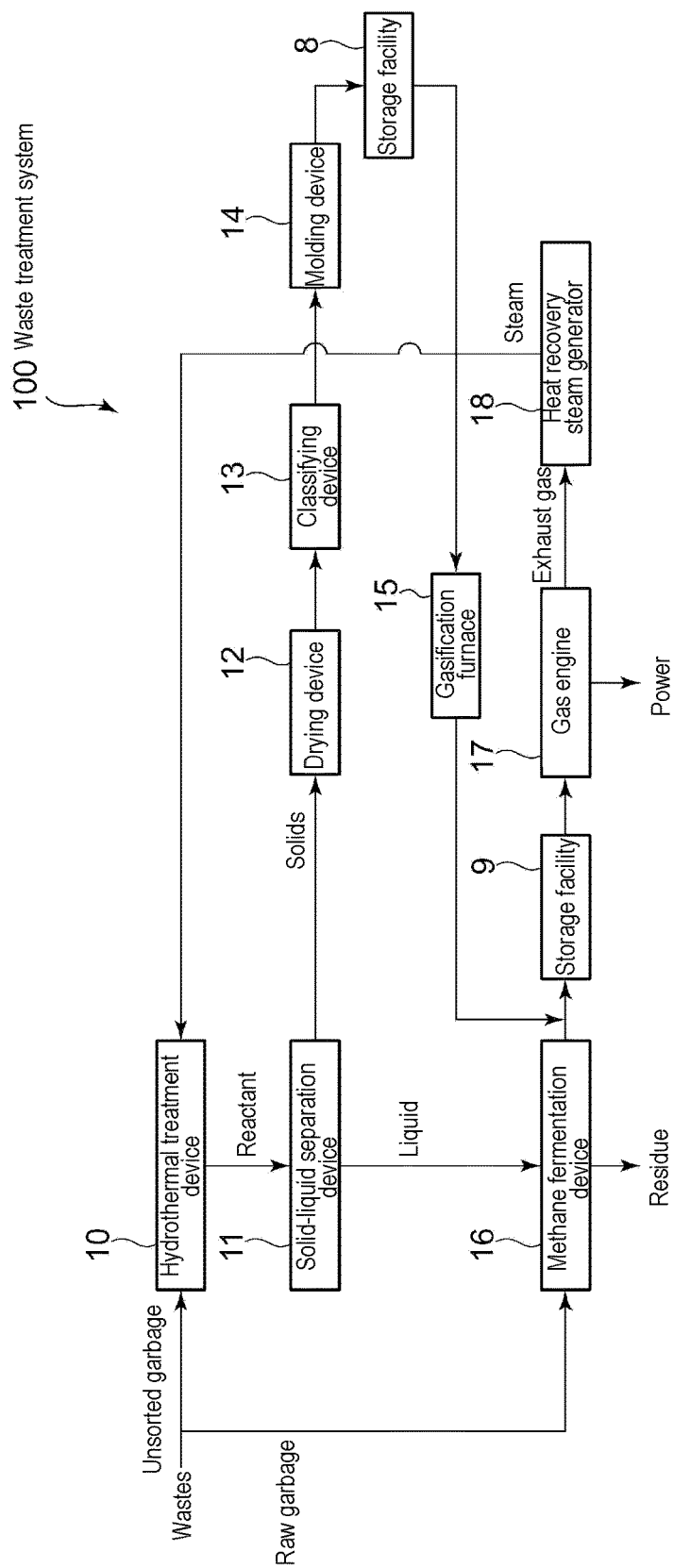
FIG. 1 is a system diagram of a waste treatment system according to the first embodiment of the present invention.

Some embodiments of the present invention will be described below with reference to the accompanying drawings. Contents described as embodiments and contents shown in the drawings below are merely examples, and can be embodied with any modification within a scope that does not depart from the present invention. Further, two or more embodiments may optionally be combined in any manner. Further, in the following embodiments, similar elements will be indicated by the same reference numerals, and redundant descriptions thereof will be omitted for convenience.

It is intended, however, that unless particularly identified, dimensions, materials, shapes, relative positions and the like of constituent components described as the embodiments or shown in the drawings shall be interpreted as illustrative only and not intended to limit the scope of the present invention.

For instance, an expression of relative or absolute arrangement such as "in a direction", "along a direction", "parallel", "orthogonal", "centered", "concentric" and "coaxial" shall not be construed as indicating only the arrangement in a strict literal sense, but also includes a state where the arrangement is relatively displaced by a tolerance, or by an angle or a distance whereby it is possible to achieve the same function.

For instance, an expression of an equal state such as "same", "equal", and "uniform" shall not be construed as indicating only the state in which the feature is strictly equal, but also includes a state in which there is a tolerance or a difference that can still achieve the same function.

Further, for instance, an expression of a shape such as a rectangular shape or a cylindrical shape shall not be construed as only the geometrically strict shape, but also includes a shape with unevenness or chamfered corners within the range in which the same effect can be achieved.

On the other hand, the expressions "comprising", "including", "having", "containing", and "constituting" one constituent component are not exclusive expressions that exclude the presence of other constituent components.

FIG. 1 is a system diagram of a waste treatment system 100 according to the first embodiment of the present invention. The waste treatment system 100 is a system for performing a hydrothermal treatment of wastes. The waste treatment system 100 includes a hydrothermal treatment device 10 (fuel production device) for performing the above-described hydrothermal treatment, a solid-liquid separation device 11 (fuel production device), a drying device 12 (fuel production device), a classifying device 13 (fuel production device), a molding device 14 (fuel production device), a storage facility 8, a gasification furnace 15, a methane fermentation device 16, a storage facility 9, a gas engine 17, and a heat recovery steam generator 18. A description of each device will be given below while describing a flow of each component derived from the wastes.

Wastes (for example, wastes including an organic matter; more specifically, for example, wastes including biomass) treated in the waste treatment system 100 undergo a hydrothermal treatment in the hydrothermal treatment device 10. More specifically, in the hydrothermal treatment device 10, the above-described hydrothermal treatment is performed by bringing steam (water vapor; the same shall apply hereinafter) into contact with the wastes (unsorted garbage is illustrated in FIG. 1). The steam used for the hydrothermal treatment is supplied from the heat recovery steam generator 18 to be described later.

The hydrothermal treatment device 10 includes, for example, a batch hydrothermal treatment device. Thus, for example, it is possible to load the wastes to the hydrothermal treatment device 10 directly from a vehicle (not shown) for collecting the wastes, and to achieve pitless of the waste treatment system 100. The specific structure of the batch water treatment device can be a structure described in, for example, each of FIGS. 17, 18, and the like to be described later.

Conditions for the hydrothermal treatment are not particularly limited. For example, the conditions can be a temperature of not less than 140° C. and not more than 250° C., a pressure of not less than 1.5 Mpa to 2.5 Mpa, and a reaction time of not less than 15 minutes and not more than 2 hours.

A reactant obtained by the hydrothermal treatment is supplied to the solid-liquid separation device 11 (fuel production device). The solid-liquid separation device 11 is constituted by, for example, a filtering device, a centrifugal separator, or the like. In the solid-liquid separation device 11, the reactant obtained by the hydrothermal treatment is separated into respective components of solids and a liquid.

The separated solids are fueled by a fuel production device for producing a solid fuel from the solids of the reactant of the hydrothermal treatment. More specifically, the separated solids are sufficiently dried by the drying device 12 (fuel production device) for drying the solids of the moisture-containing solid reactant obtained in the hydrothermal treatment device 10 (fuel production device). Thus, it is possible to produce the combustible solid fuel (granular dry matters) by drying the reactant of the hydrothermal treatment. Moreover, in a case in which an inorganic component such as metal is mixed besides the dry matters, the inorganic component is removed in a separator (fuel production device) (not shown). Then, in the classifying device 13 (fuel production device), using, for example, a sieve, dry matters are sorted with respect to each similar size, and the dry matters which are large in grain size are recycled to the hydrothermal treatment device 10 again.

As another implementation method, it is also possible to install a pulverization facility at an outlet of the solid-liquid separation device or an outlet of the drying device, in order to fine the dry matters which are large in grain size.

Lastly, in the molding device 14 (fuel production device), the dry matters of each size are mixed to be about an equal amount, and then molded. At this time, the molding may be performed by using a binder. That is, the molding may be performed by bringing the mixture and the binder into contact with each other. As the binder, for example, lignin, starch, or the like can be used. Thus, the dry matters are bound, obtaining a fuel pellet (solid fuel) which is a pellet-like fuel. The fuel pellet is stored in the storage facility 8 (for example, a bunker; first storage facility) for storing the solid fuel produced from the reactant of the hydrothermal treatment.

Since the fuel pellet is thus produced from the above-described solid reactant, it is possible to store the fuel as the pellet and to combust the fuel in accordance with a power demand. Moreover, producing the fuel pellet by using the binder, it is possible to fill a void included in the fuel pellet with the binder. Thus, it is possible to reduce a contact area with air in the fuel pellet and to enhance storage stability.

The fuel pellet thus produced may be shipped as a product, in addition to being stored as described above.

The fuel pellet stored in the storage facility 8 is extracted in accordance with the amount of steam required in the hydrothermal treatment device 10, and is steamed and roasted at a high temperature in the gasification furnace 15 (for example, a fluidized bed) for gasifying the fuel pellet (solid fuel) to generate a fuel gas. Consequently, the fuel gas containing hydrogen, carbon monoxide, and the like is generated. The fuel gas is stored in the storage facility 9 (for example, a gas holder; the second storage facility, the third storage facility) for storing the fuel gas generated in the gasification furnace 15. Including the storage facilities 8, 9, it is possible to store both the solid fuel and the fuel gas generated from the solid fuel.

On the other hand, the liquid separated in the above-described solid-liquid separation device 11 is supplied to the methane fermentation device 16. Moreover, biomass (raw garbage is illustrated in FIG. 1) included in the above-described wastes is also supplied to the methane fermentation device 16. The methane fermentation device 16 is a device for performing methane fermentation on the biomass and is, for example, a fermenter for accommodating a methanogenic bacteria. Therefore, in the methane fermentation device 16, the methane fermentation of the biomass and the above-described liquid is performed. Consequently, a biogas is generated. Note that methane fermentation can be performed, for example, under an anaerobic condition of not less than 30° C. and not more than 60° C., or preferably not less than 50° C. and not more than 60° C.

The biogas generated in the methane fermentation device 16 is a gas containing at least methane and is, more specifically, a mixed gas containing methane and carbon dioxide, for example. The biogas is discharged from the methane fermentation device 16. Thus, the biogas is purified by a purifier (not shown), and the purified gas is stored in the above-described storage facility 9 (for example, the gas holder; the second storage facility, the third storage facility). Including the storage facilities 8, 9, it is possible to store both the solid fuel and the biogas (for example, methane) generated from the reactant of the hydrothermal treatment. The biogas and the fuel gas generated in the above-described gasification furnace 15 are stored in the same storage facility 9 together. However, the biogas and the fuel gas may be stored in different storage facilities. On the other hand, a residue after the methane fermentation in the methane fermentation device 16 is discharged from the methane fermentation device 16, and undergoes incineration treatment or is used as compost, for example.

The biogas and fuel gas stored in the storage facility 9 are supplied to the gas engine 17 (power generation device). The gas engine 17 is connected to a generator body part (power generation device) (not shown). Thus, the generator body part generates power by using a combustion energy generated by combustion of the biogas and the fuel gas supplied to the gas engine 17. Thus, it is possible to generate power by using the fuel produced in the waste treatment system 100.

In particular, the fuel gas generated in the gasification furnace 15 is also supplied to the gas engine 17, as described above. Thus, in the gas engine 17, the fuel gas generated in the gasification furnace 15 is also combusted, in addition to the above-described methane. Therefore, the generator body part (power generation device) connected to the gas engine 1 generates power by combusting the fuel gas, which is generated from the reactant (fuel pellet) of the hydrothermal treatment device 10 described above, in the gasification furnace 15.

More specifically, the generator body part (power generation device) generates power by using the combustion energy generated by combustion of the fuel in a fluidized-bed furnace (gasification furnace 15). Thus, with the fluidized-bed furnace, it is possible to combust the fuel pellet rapidly while suppressing a variation in combustion. Thus, it is possible to generate power rapidly while suppressing a variation in power generation amount.

In the above example, the fuel pellet is combusted in the gasification furnace 15. However, for example, the dry matters obtained by the drying device 12 are stored, and may be combusted in the gasification furnace 15 in place of the above-described fuel pellet or together with the above-described fuel pellet. Combusting the dry matters before being molded, it is possible to reduce a time and cost associated with molding.

An exhaust gas discharged from the gas engine 17 is supplied to the heat recovery steam generator 18. The heat recovery steam generator 18 (steam generation device) is a device for generating steam to be supplied to the above-described hydrothermal treatment device 10. Then, the heat recovery steam generator 18 generates steam by using the combustion energy generated by fuel combustion, that is, heat (may be a part thereof) of the exhaust gas.

The fuel here includes a fuel gas generated by steaming and roasting the fuel pellet stored in the storage facility 8 at the high temperature in the gasification furnace 15, besides the biogas generated in the methane fermentation device 16. In particular, the fuel pellet is converted into the fuel gas in the gasification furnace 15, and the fuel gas is further combusted in the gas engine 17 and is converted into the combustion energy. Therefore, the combustion energy for generating steam is obtained by the gas generated in the gasification furnace 15.

Thus, it is possible to generate steam by using the combustion energy of the fuel derived from the wastes. Then, the generated steam is supplied to the above-described hydrothermal treatment device 10. In the hydrothermal treatment device 10, the hydrothermal treatment is performed by using the supplied steam.

In particular, in the heat recovery steam generator 18, steam is generated by using at least the combustion energy generated by combusting the methane, which is generated in the methane fermentation device 16, in the gas engine 17 as described above. Thus, it is possible to combust the methane generated through methane fermentation of biomass. Thus, it is possible to increase a heating value and to increase a steam generation amount.

Furthermore, in the heat recovery steam generator 18, steam is generated by using the combustion energy in the gasification furnace 15 constituted by the fluidized-bed furnace for combusting the fuel, as described above. Thus, with the fluidized-bed furnace, it is possible to combust the fuel rapidly while suppressing the variation in combustion. Thus, it is possible to generate steam rapidly while suppressing a variation in generation amount.

According to the waste treatment system 100, it is possible to generate steam to be used in the hydrothermal treatment device 10, by using the fuels obtained from the wastes and stored in the storage facilities 8, 9. Thus, it is possible to change the steam amount in accordance with the waste amount.

Moreover, it is possible to combust, as a fuel, the gas which is generated from the solid reactant (solid content) obtained in the hydrothermal treatment device 10. Thus, it is possible to generate steam by using the combustion energy and to use the generated steam in the hydrothermal treatment device 10. As a result, it is possible to reduce the amount of steam externally supplied to the hydrothermal treatment device 10. Moreover, it is possible to generate power by using the above-described combustion energy. Accordingly, it is possible to use the wastes as the fuel more effectively.

Moreover, using the above-described waste treatment system 100, it is possible to perform the hydrothermal treatment of the wastes, as described above. That is, a waste treatment method according to an embodiment of the present invention includes a hydrothermal treatment step of performing a steam hydrothermal treatment by bringing steam into contact with the above-described wastes. The hydrothermal treatment step can be performed by, for example, the above-described hydrothermal treatment device 10. Moreover, the waste treatment method according to an embodiment of the present invention includes a storage step of storing the fuel produced from the reactant of the above-described hydrothermal treatment (the reactant in the hydrothermal treatment step). The fuel stored in the storage step is stored in the above-described storage facility 8, 9 by, for example, transportation equipment or the like.

Furthermore, the waste treatment method according to an embodiment of the present invention includes a steam generation step of generating the above-described steam to be used in the above-described hydrothermal treatment step. The steam generation step can be performed by, for example, the above-described heat recovery steam generator 18. Then, the steam generation step generates the above-described steam by using the combustion energy generated by combustion of the fuels (the fuel pellet, methane, the fuel gas generated by gasification of the fuel pellet, and the like) stored in the above-described storage step.

According to the above waste treatment method, it is possible to generate steam to be used in the hydrothermal treatment device 10, by using the fuels obtained from the wastes and stored in the storage facilities 8, 9. Thus, it is possible to change the steam amount in accordance with the waste amount. Note that the exhaust gas after steam generation in the heat recovery steam generator 18 may partially be supplied to the drying device 12 to be used as one of heat sources for drying a solid matter generated in the hydrothermal treatment device 10. Thus, it is possible to reduce the energy used for drying.

Moreover, it is possible to combust, as a fuel, at least one of the solid reactant (solid content) obtained in the hydrothermal treatment step or the gas generated from the solid content. Thus, it is possible to generate steam by using the combustion energy and to use the generated steam in the hydrothermal treatment step. As a result, it is possible to reduce the amount of steam externally supplied to the hydrothermal treatment step. Moreover, it is possible to generate power by using the above-described combustion energy. Accordingly, it is possible to use the wastes as the fuel more effectively.

Figure 2:
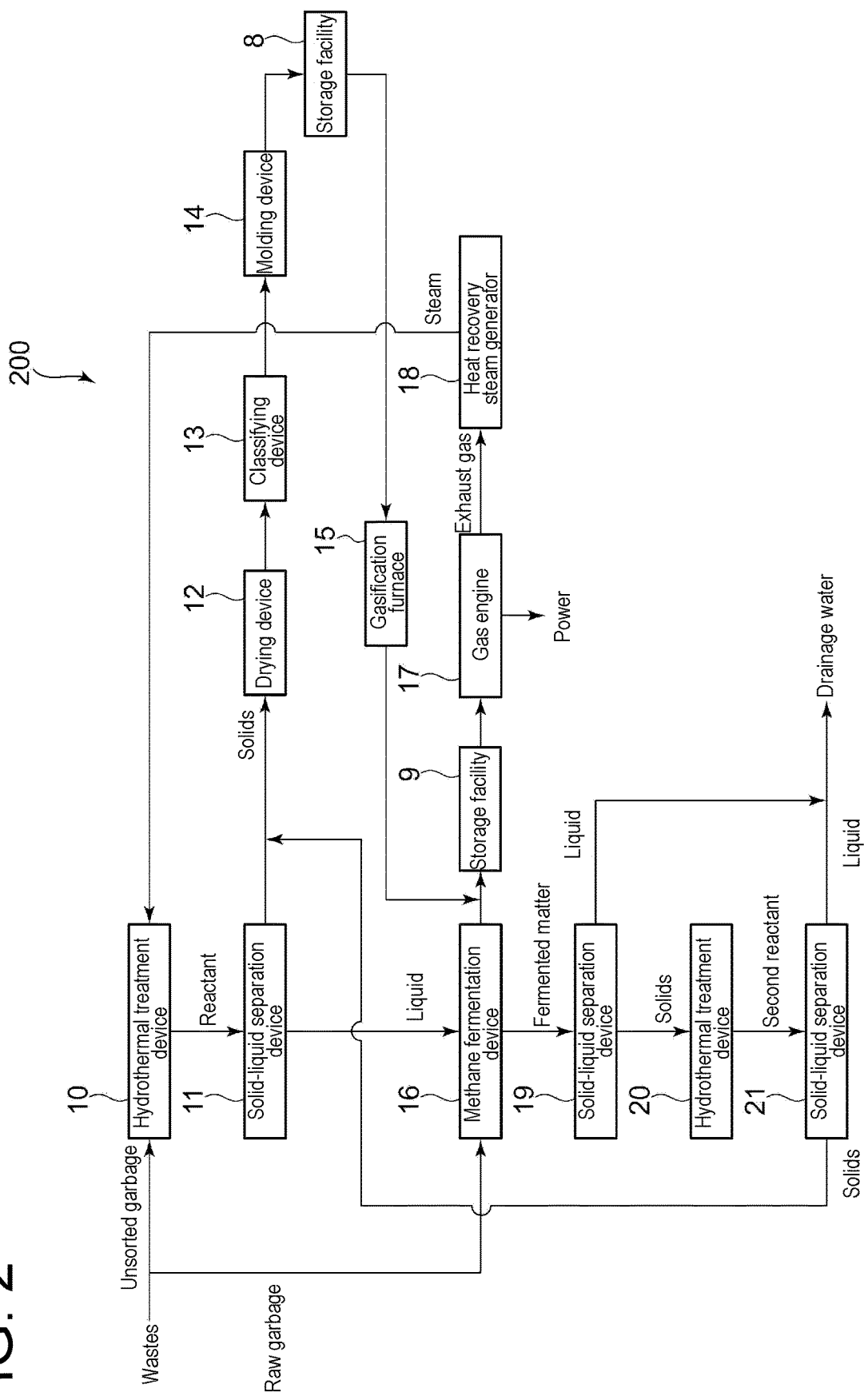
FIG. 2 is a system diagram of a waste treatment system according to the second embodiment of the present invention.

FIG. 2 is a system diagram of a waste treatment system 200 according to the second embodiment of the present invention. In the waste treatment system 200, the hydrothermal treatment is performed on the residue generated in the methane fermentation device 16 of the waste treatment system 100 described above. The waste treatment system 200 includes a solid-liquid separation device 19, a hydrothermal treatment device 20 (second hydrothermal treatment device), and a solid-liquid separation device 21. The solid-liquid separation device 19 is a device for performing solid-liquid separation on a fermented matter obtained in the methane fermentation device 16. The hydrothermal treatment device 20 is a device for performing a hydrothermal treatment by bringing steam into contact with solids (digestive sludge) in the fermented matter obtained in the methane fermentation device. The solid-liquid separation device 21 is a device for performing solid-liquid separation on the second reactant obtained in the hydrothermal treatment device 20.

Moreover, as another implementation method, it is also possible to recycle the solids (digestive sludge) obtained in the solid-liquid separation device 19 to the hydrothermal treatment device 10. In this case, the hydrothermal treatment device 20 and the solid-liquid separation device 21 are not needed.

As with the above-described hydrothermal treatment device 10, the hydrothermal treatment device 20 also includes, for example, the batch hydrothermal treatment device. The specific structure of the batch water treatment device can be the structure described in, for example, each of FIGS. 17, 18, and the like to be described later.

The fermented matter obtained in the methane fermentation device 16 undergoes solid-liquid separation by the solid-liquid separation device 19. The solid-liquid separation device 19 is constituted by, for example, the filtering device, the centrifugal separator, a gravity separator (thickener) or the like. The component (digestive sludge) of the solids separated by the solid-liquid separation device 19 is supplied to the hydrothermal treatment device 20.

The component of the solids (digestive sludge) supplied to the hydrothermal treatment device 20 undergoes the hydrothermal treatment. Conditions for the hydrothermal treatment can be the same as, for example, the conditions for the hydrothermal treatment in the hydrothermal treatment device 10 described above. Note that the steam from the heat recovery steam generator 18 described above may be supplied to the hydrothermal treatment device 20.

Then, the second reactant obtained in the hydrothermal treatment device 20 undergoes solid-liquid separation by the solid-liquid separation device 21. The solid-liquid separation device 21 is constituted by, for example, the filtering device, the centrifugal separator, the gravity separator (thickener) or the like. The component of the solids separated in the solid-liquid separation device 21 is supplied to the above-described drying device 12, together with the component of the solids separated by the above-described solid-liquid separation device 11. Then, the supplied second reactant is fueled together with the solids separated in the solid-liquid separation device 11 described above. Therefore, in the waste treatment system 200, the storage facility 8 is configured to store the fuel produced from the second reactant of the hydrothermal treatment in the hydrothermal treatment device 20.

Thus, with the hydrothermal treatment device 20, it is possible to perform a further hydrothermal treatment on the fermented matter. Thus, dehydration efficiency is improved by micronizing the second treated object that has undergone the hydrothermal treatment in the hydrothermal treatment device 20. Consequently, it is possible to easily perform solid-liquid separation in the solid-liquid separation device 21, and to easily produce the fuel.

Moreover, as with the liquid separated by the solid-liquid separation device 19 described above, the liquid separated in the solid-liquid separation device 21 is water having relatively high purity, as well. Thus, the component of the liquid separated by the solid-liquid separation device 21 is directly drained, as well.

In the waste treatment system 200, the solid content (solid component) of the second reactant obtained in the hydrothermal treatment device 20 is supplied to the above-described drying device 12, as described above. Therefore, in the waste treatment system 200, steam is generated in the heat recovery steam generator 18 by using a combustion energy generated by combustion of the solid second reactant obtained by the hydrothermal treatment device 20.

According to the waste treatment system 200, it is possible to further increase the heating value by the combustion of the solid second reactant obtained by the hydrothermal treatment device 20. Thus, it is possible to further increase the steam generation amount. Moreover, with the hydrothermal treatment device 20, the dehydration efficiency is improved by micronizing the product material of the hydrothermal treatment. Consequently, it is possible to easily separate moisture from the second reactant. As a result, the second reactant is combusted easily, making it possible to increase the heating value.

Note that the gasification furnace 15 may not be provided in FIG. 2. In this case, the fuel pellet stored in the storage facility 8 can be used as, for example, an industrial product, as needed.

Furthermore, the solid-liquid separation device 21 may not be provided in FIG. 2. That is, the hydrothermal treatment in the hydrothermal treatment device 20 can be performed at a high temperature exceeding 100° C., as described above. Thus, it is possible to efficiently dry the second reactant in the hydrothermal treatment device 20 by hydrothermally treating the digestive sludge to micronize the sludge, and then evaporating water contained in the digestive sludge, in the hydrothermal treatment device 20. That is, the hydrothermal treatment device 20 is configured to dry the second reactant obtained in the hydrothermal treatment device 20. Then, the second reactant obtained here may be supplied to a portion between the drying device 12 and the classifying device 13. Thus, the hydrothermal treatment device 20 itself that has performed the hydrothermal treatment can dry the second reactant obtained by the hydrothermal treatment. Moreover, it is possible to reduce the amount of the solids treated in the drying device 12, and to downsize the drying device 12.

Moreover, in FIG. 2, specific gravity separation may be performed on the fermented matter of the methane fermentation device 16. In this case, the digestive sludge including many organic matters is accumulated underneath, and a supernatant liquid including little organic matter is accumulated at the top. The supernatant liquid can be drained.

Figure 3:
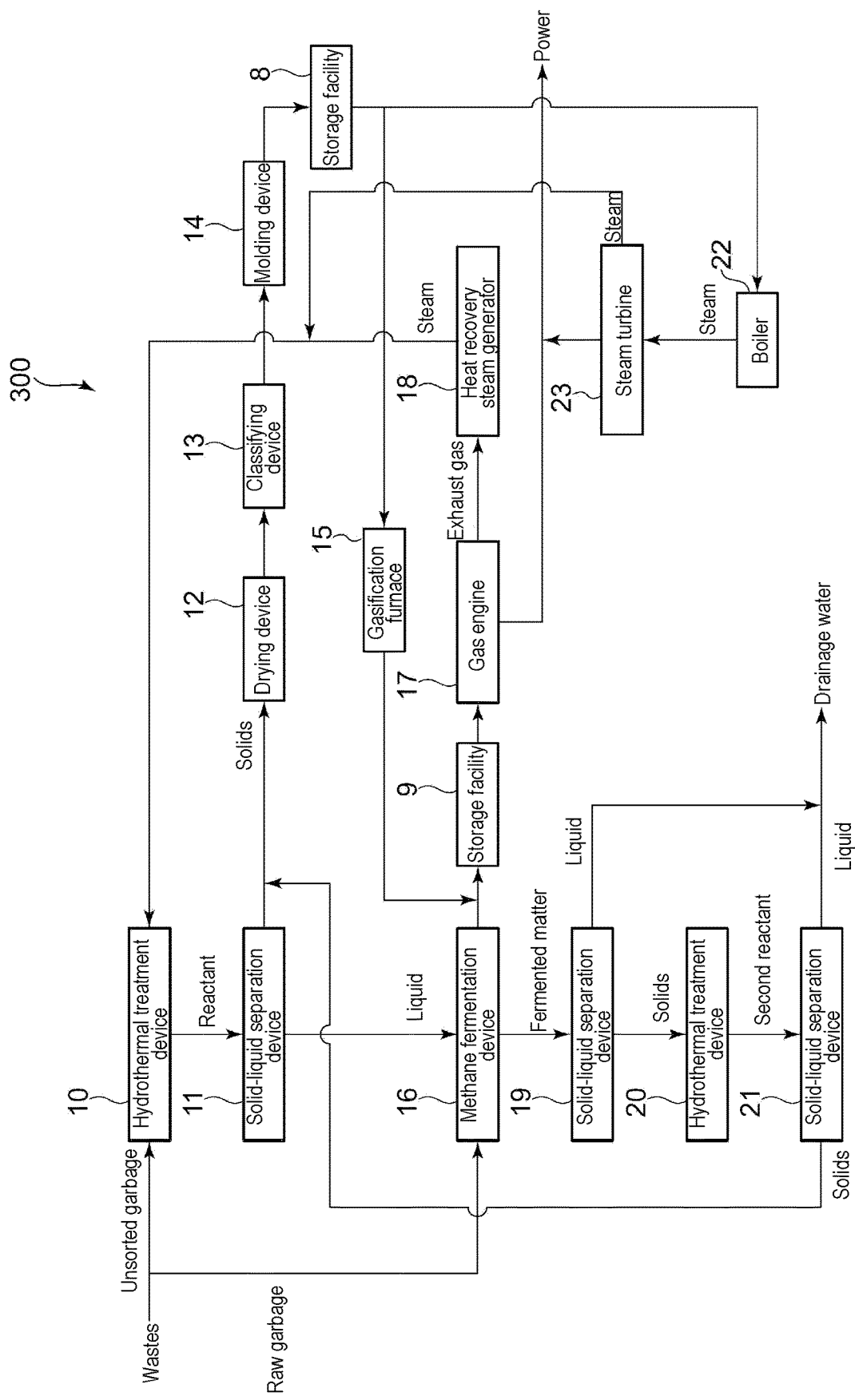
FIG. 3 is a system diagram of a waste treatment system according to the third embodiment of the present invention.

FIG. 3 is a system diagram of a waste treatment system 300 according to the third embodiment of the present invention. The waste treatment system 300 generates power by generating steam by combustion of the fuel pellet in a boiler 22 to drive a steam turbine 23 in the above-described waste treatment system 200 (see FIG. 2).

The waste treatment system 300 includes the boiler 22 (steam generation device), the steam turbine 23, and the generator body part (not shown) connected to the steam turbine 23. Of the above constituent components, the boiler 22 is provided to combust the fuel pellet stored in the storage facility 8 as a fuel. Combusting the fuel pellet (fuel), steam is generated. Moreover, the steam turbine 23 (power generation device) is driven by the steam (can be at least a part thereof) generated in the boiler 22. Moreover, the generator body part (power generation device) connected to the steam turbine 23 is a device for generating power by driving the steam turbine 23.

The fuel pellet stored in the storage facility 8 is combusted in the boiler 22, in addition to being gasified in the gasification furnace 15 as described above. Then, in the boiler 22, steam is generated by combustion of the fuel pellet, and the steam turbine 23 is driven by the generated steam. Thus, the generator body part connected to the steam turbine 23 generates power to be extracted. That is, the steam drives the steam turbine 23, and the generator body part connected to the steam turbine 23 can generate power. In this example, the fuel pellet is combusted in the boiler 22. However, for example, the dry matters obtained by the drying device 12 may be combusted in the boiler 22 in place of the above-described fuel pellet or together with the above-described fuel pellet. Combusting the dry matters before being molded, it is possible to reduce the time and cost associated with molding.

On the other hand, the steam supplied to the steam turbine 23 is extracted in the middle of the steam turbine 23 and supplied to the hydrothermal treatment device 10. The steam supplied to the steam turbine 23 may be supplied to the hydrothermal treatment device 20.

According to the waste treatment system 300, the steam drives the steam turbine 23, and it is possible to generate power by the generator body part connected to the steam turbine 23. Then, since the steam supplied to the steam turbine 23 is supplied to the hydrothermal treatment device 10, it is possible to perform the hydrothermal treatment by using the steam generated in the boiler 22.

Moreover, in the waste treatment system 300, the power generation device includes the gas engine 17 (power generation device; first power generation device) and the steam turbine 23 (power generation device; second power generation device). Thus, it is possible to optionally change the number of power generation devices used, in accordance with the power demand. Thus, it is possible to flexibly change the power generation amount in accordance with the power demand, and to stably supply power.

Moreover, in the boiler 22, the fuel pellet, which is the solid reactant in the hydrothermal treatment device 10, is combusted. In the hydrothermal treatment device 10, since a salt is contained on a liquid side, a salt concentration on a solid side is reduced sufficiently. Thus, it is possible to suppress entry of salt into the boiler 22 and to suppress corrosion of the boiler 22, when the fuel pellet is combusted in the boiler 22.

When the fuel pellet is supplied to the boiler 22, the fuel pellet can be supplied to the vicinity of the center of a stoker (not shown) in the boiler 22. Thus, it is possible to rapidly combust the fuel pellet. Moreover, although not shown, in a case in which the wastes are also supplied to the boiler 22, it is preferable that the supply amount of the fuel pellet is adjusted in accordance with a water content of the wastes to equalize the amount of water entering the boiler 22.

Figure 4:
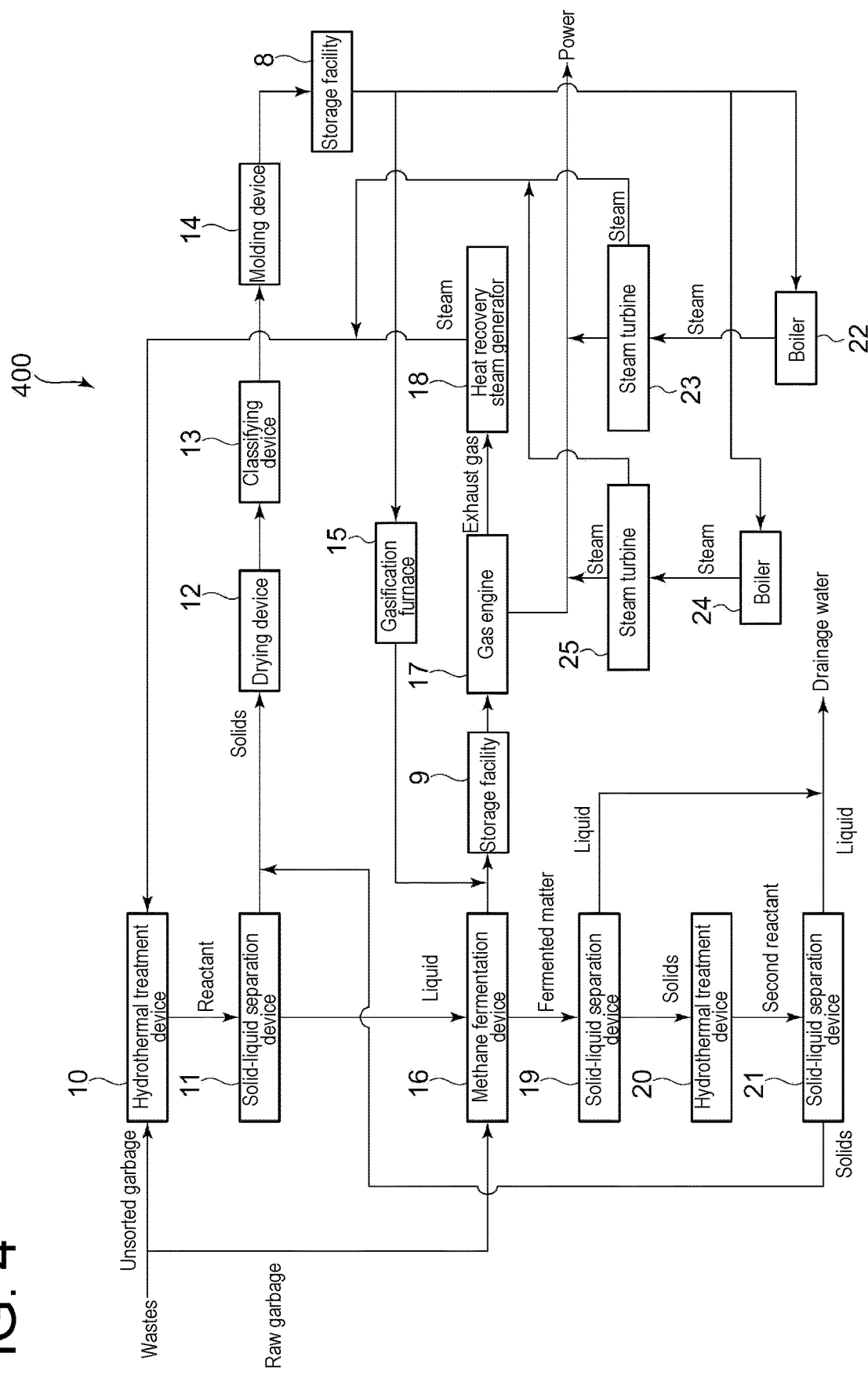
FIG. 4 is a system diagram of a waste treatment system according to the fourth embodiment of the present invention.

FIG. 4 is a system diagram of a waste treatment system 400 according to the fourth embodiment of the present invention. The waste treatment system 400 includes three power generation devices in the above-described waste treatment system 300 (see FIG. 3). More specifically, in the waste treatment system 400, a steam turbine 25 (power generation device; third power generation device) is provided, in addition to the above-described gas engine 17 (power generation device; first power generation device) and the steam turbine 23 (power generation device; second power generation device). The steam turbine 25 is connected to the generator body part (not shown). Moreover, the waste treatment system 400 includes a boiler 24 for supplying steam to the steam turbine 25. Note that there may be not less than four power generation devices.

In the waste treatment system 400, the gas engine 17 generates power by using the gas generated from the fuel pellet, as described above. Moreover, the fuel pellet is also combusted in the boiler 24 as needed, in addition to being combusted in the boiler 22 as described above. Thus, steam generated in the boiler 24 drives the steam turbine 25, and power is generated in the generator body part connected to the steam turbine 25. Moreover, as with the steam in the steam turbine 23 described above, the steam in the steam turbine 25 is supplied to the hydrothermal treatment device 10.

According to the waste treatment system 400, it is possible to optionally change the number of power generation devices (the boilers and the steam turbines) used, in accordance with the power demand. Thus, it is possible to flexibly change the power generation amount in accordance with the power demand, and to stably supply power. More specifically, for example, on the basis of power generation by the gas engine 17, it is possible to make parallel use of the boiler 22 and the steam turbine 23, in accordance with a daily change in power demand (for example, a change in power demand between day and night). Then, for example, it is possible to make further parallel use of the boiler 24 and the steam turbine 25, in accordance with a seasonal change in power demand.

Figure 5:
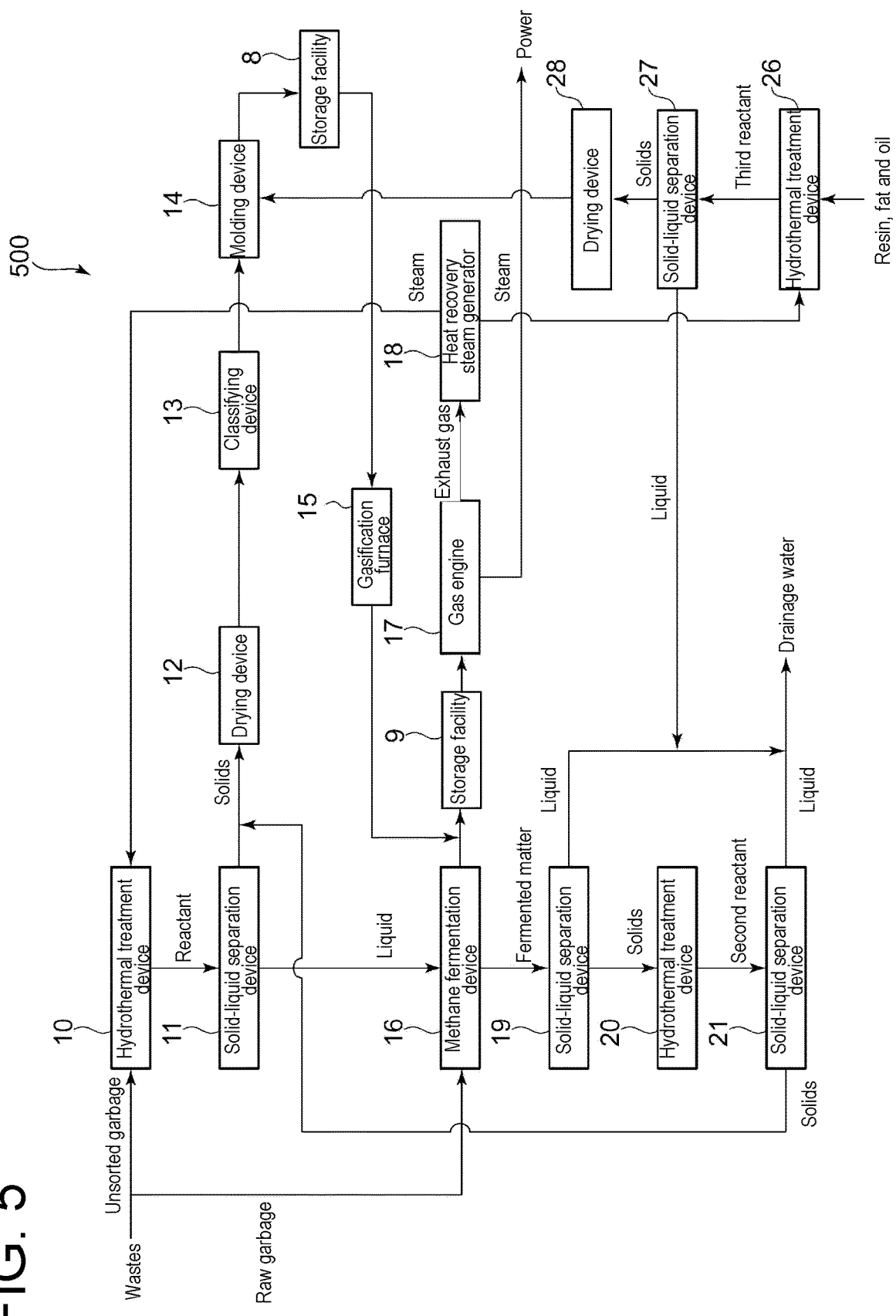
FIG. 5 is a system diagram of a waste treatment system according to the fifth embodiment of the present invention.

FIG. 5 is a system diagram of a waste treatment system 500 according to the fifth embodiment of the present invention. The waste treatment system 500 generates the binder used to produce the fuel pellet in the above-described waste treatment system 200 (see FIG. 2) from wastes such as a resin, an oil and a fat. FIG. 5 shows a hydrothermal treatment device 26 to produce the binder. However, without using the hydrothermal treatment device 26, the resin or the oil and the fat may be supplied to the hydrothermal treatment device 10.

The waste treatment system 500 includes the hydrothermal treatment device 26 (third hydrothermal treatment device) for obtaining the third reactant by the hydrothermal treatment of the wastes containing at least one of the resin or the oil and the fat. The resin or the oil and the fat here are, for example, a resin such as plastic, or an oil and a fat obtained by separating POME (Palm Oil Mill Effluent) or the like into an oil and water.

Conditions for the hydrothermal treatment in the hydrothermal treatment device 26 can be the same as the conditions for the hydrothermal treatment in the hydrothermal treatment device 10 described above. Moreover, in the hydrothermal treatment device 26, the hydrothermal treatment may be performed by using the steam supplied from the heat recovery steam generator 18, or the hydrothermal treatment may be performed by using the steam supplied from the steam generation device (not shown) other than the heat recovery steam generator 18. Furthermore, as with the above-described hydrothermal treatment device 10, the hydrothermal treatment device 26 also includes, for example, the batch hydrothermal treatment device. The specific structure of the batch water treatment device can be the structure described in, for example, each of FIGS. 17, 18, and the like to be described later.

Performing the hydrothermal treatment of the wastes containing at least one of the resin or the oil and the fat, the third reactant is obtained. Then, performing solid-liquid separation of the third reactant in a solid-liquid separation device 27 (the same device as the above-described solid-liquid separation device 11 can be adopted), the solid third reactant is obtained. On the other hand, the liquid third reactant is drained directly. The solid third reactant obtained in the solid-liquid separation device 27 is derived from the wastes containing at least one of the resin or the oil and the fat. Thus, the third reactant has a relatively high viscosity. Therefore, the solid third reactant is dried by a drying device 28 (the same device as the above-described drying device 12 can be adopted), and then supplied to the molding device 14 as a binder.

Then, in the molding device 14, the fuel pellet is produced by bringing the above-described dry matter and the binder in to contact with each other. Therefore, in the waste treatment system 500, the fuel production device, which includes the hydrothermal treatment device 10, the solid-liquid separation device 11, the drying device 12, the classifying device 13, and the molding device 14, is configured to produce the fuel pellet (solid fuel) by using the third reactant.

According to the waste treatment system 500, it is possible to easily mold the fuel pellet by using the third reactant obtained by the hydrothermal treatment device 26 as the binder, and to produce the solid fuel.

Figure 6:
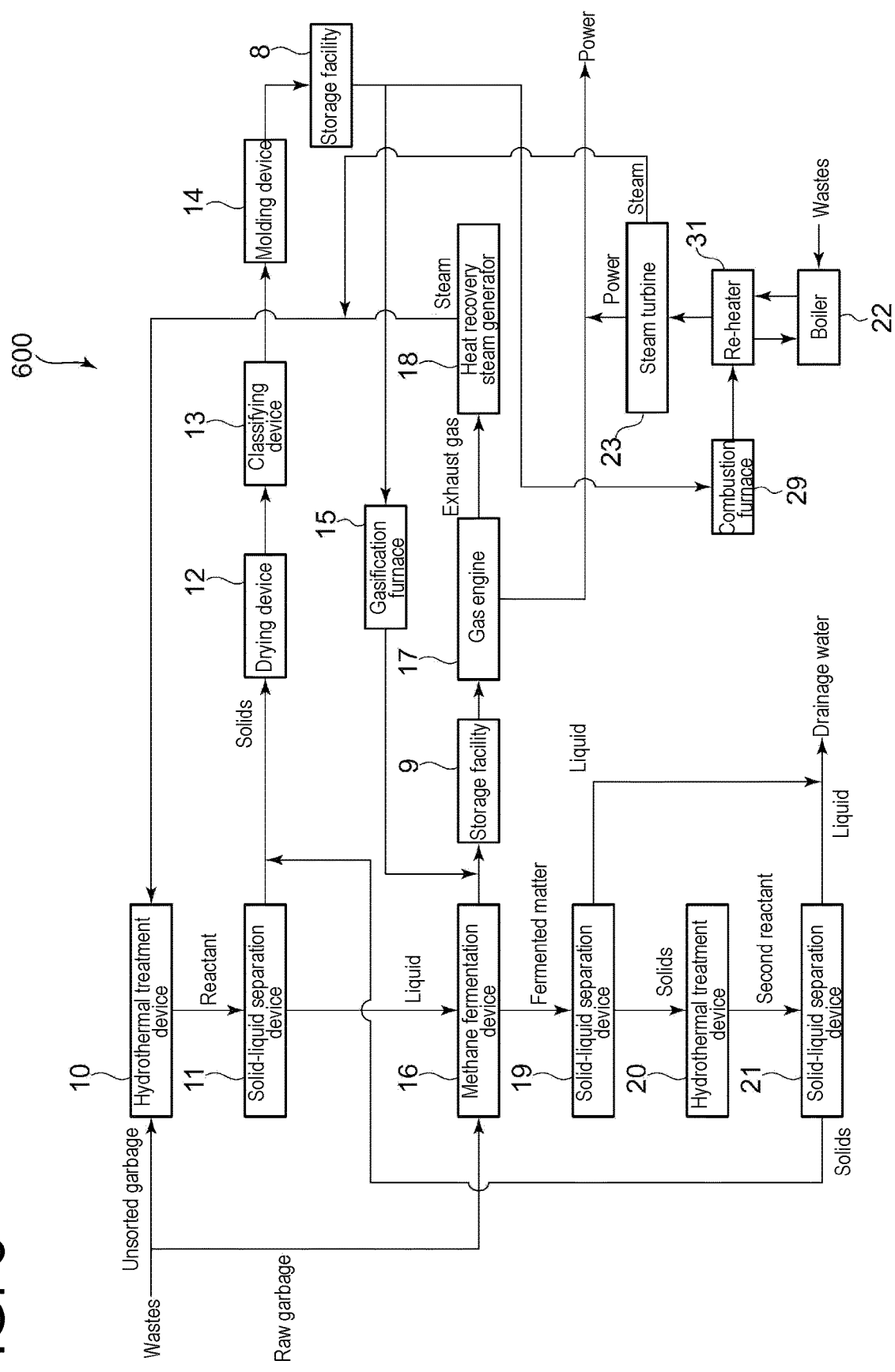
FIG. 6 is a system diagram of a waste treatment system according to the sixth embodiment of the present invention.

FIG. 6 is a system diagram of a waste treatment system 600 according to the sixth embodiment of the present invention. The waste treatment system 600 is a system for increasing the temperature of the steam to be supplied to the steam turbine 23 from the boiler 22 for incinerating wastes, in the above-described waste treatment system 300 (see FIG. 3). The waste treatment system 600 includes a combustion furnace 29 for combusting the fuel, and a re-heater 31 for superheating the steam supplied from the boiler 22 to the steam turbine 23 by using a combustion energy generated in the combustion furnace 29. In the combustion furnace 29, the fuel pellet produced in the molding device 14 is combusted. Thus, it is possible to superheat the steam to be used in the steam turbine 23. If wastes are combusted in a garbage incinerator, the temperature of the steam generated in the boiler cannot normally be raised exceeding 400° C., due to a problem of high-temperature corrosion of a boiler tube. However, including the re-heater and biogas combustion furnace arranged independently as in the system 700, it is possible to increase the temperature of the steam to be supplied to the steam turbine to not lower than 400° C., and to improve efficiency (power generation efficiency) of the steam turbine.

If the water content of the wastes combusted in the boiler 22 is high (for example, if the wastes combusted in the boiler 22 are raw garbage), a heat quantity of the combustion gas generated in the boiler 22 decreases. As a result, the amount of the steam generated in the boiler 22 decreases, making it impossible to supply electric energy stably. Thus, a combustion amount of the biogas in the combustion furnace 29 is adjusted in accordance with the heat quantity of the combustion gas generated in the boiler 22, making it possible to stabilize the generation amount and temperature of the steam through the re-heater, and to supply electric energy stably.

Moreover, in this case, the combustion gas that has superheated the steam in the re-heater 31 is supplied to the garbage incinerator.

According to the waste treatment system 600, it is possible to supply power stably, even for the boiler 22 for combusting the wastes of high water content.

Figure 7:
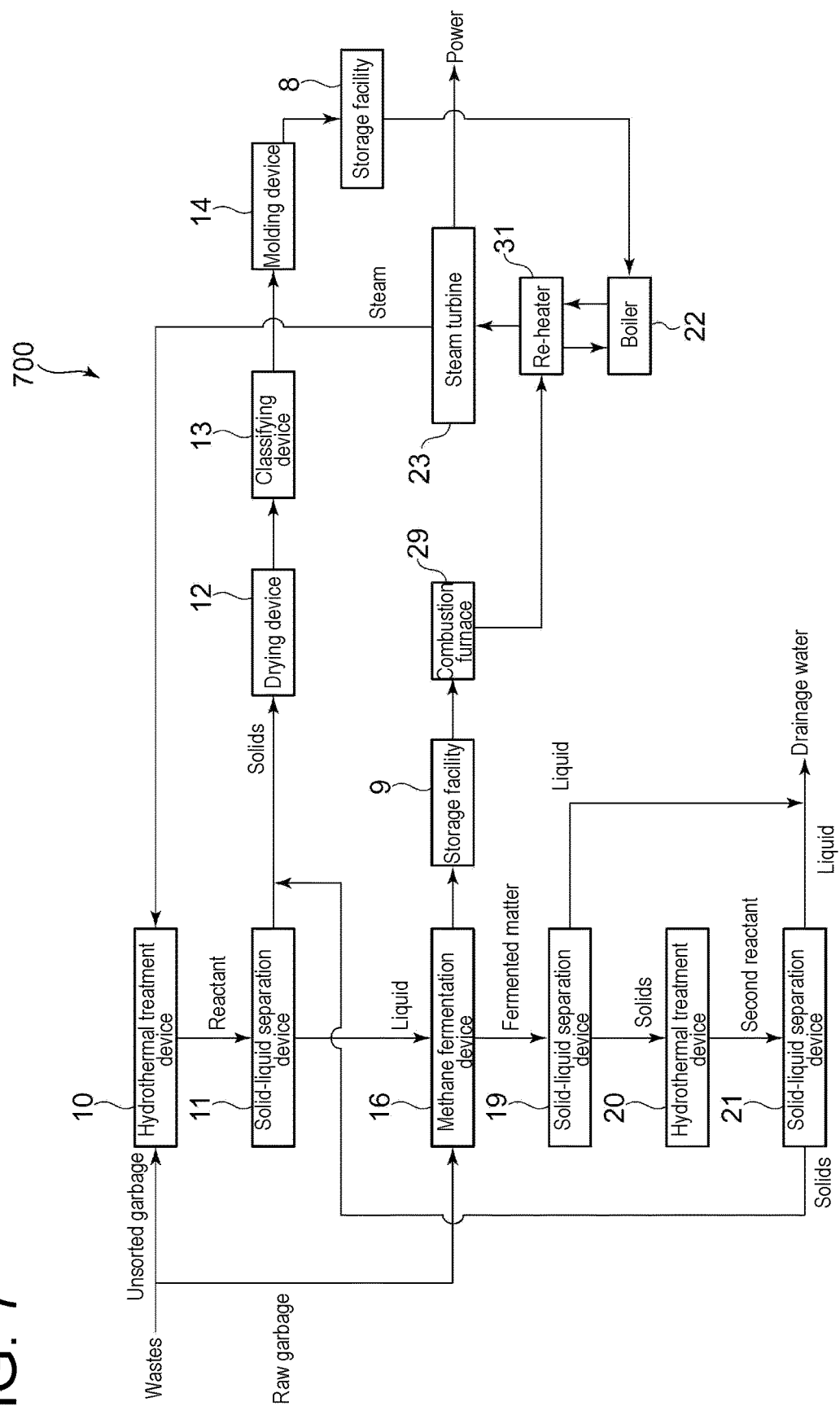
FIG. 7 is a system diagram of a waste treatment system according to the seventh embodiment of the present invention.

FIG. 7 is a system diagram of a waste treatment system 700 according to the seventh embodiment of the present invention. The waste treatment system 700 includes the boiler 22 and the steam turbine 23, in place of the gas engine 17 and the heat recovery steam generator 18, in the above-described waste treatment system 200 (see FIG. 2). Then, using the combustion energy of the biogas stored in the storage facility 9, the steam to be supplied to the steam turbine 23 is superheated.

The waste treatment system 700 includes the combustion furnace 29 for combusting the methane obtained in the methane fermentation device 16 and the re-heater 31 to which the combustion gas generated in the combustion furnace 29 is supplied, in addition to including the boiler 22 and the steam turbine 23 as described above. With the re-heater 31, it is possible to superheat the steam supplied from the boiler 22 to the steam turbine 23. Moreover, the combustion gas that has superheated the steam in the re-heater 31 is supplied to the boiler 22.

According to the waste treatment system 700, it is possible to superheat steam whose temperature is sufficiently high due to combustion of the fuel pellet, and to supply the steam in a further superheated state than in the above-described waste treatment system 600 to the boiler 22. Thus, it is possible to further improve power generation efficiency.

Figure 8:
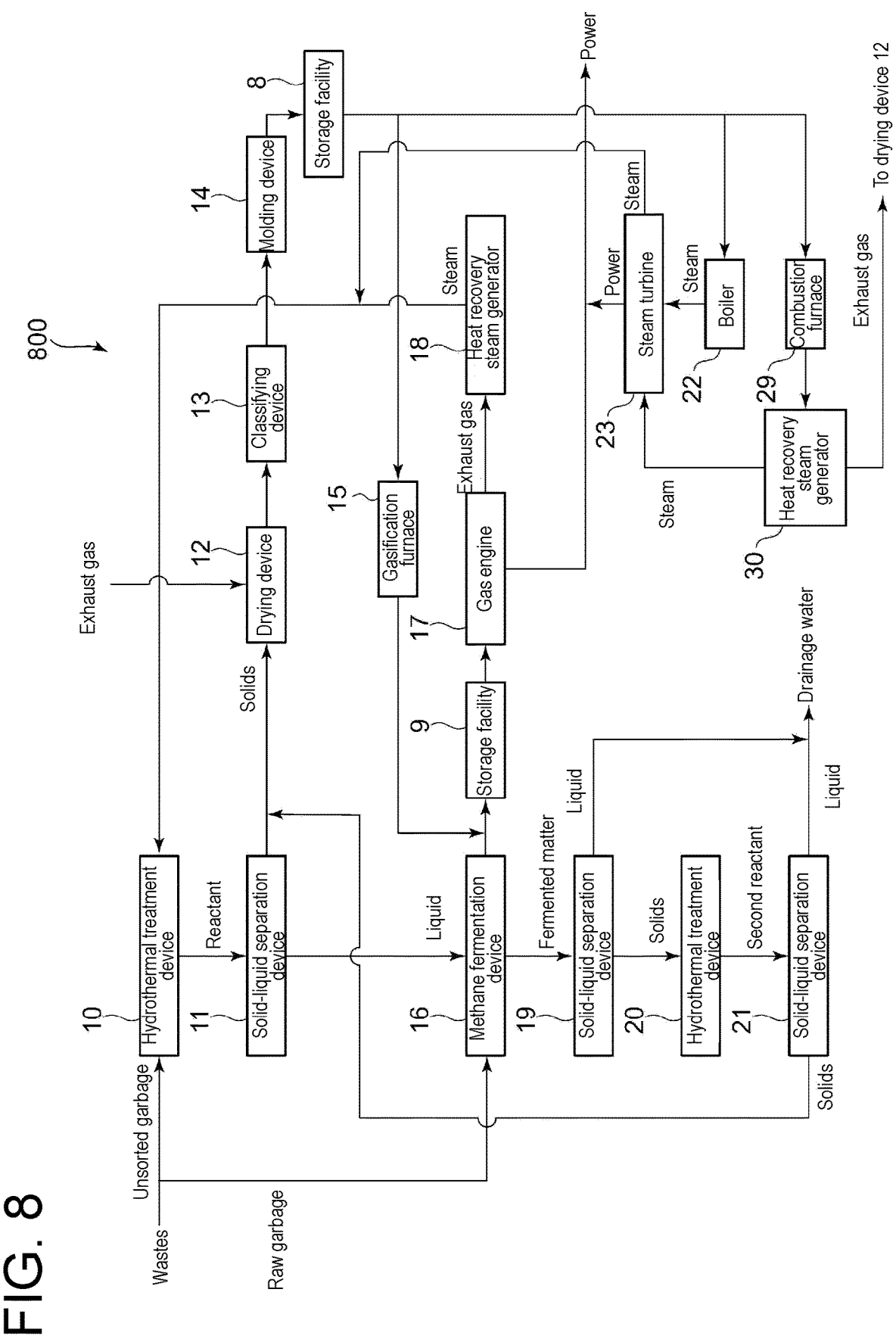
FIG. 8 is a system diagram of a waste treatment system according to the eighth embodiment of the present invention.

FIG. 8 is a system diagram of a waste treatment system 800 according to the eighth embodiment of the present invention. In the waste treatment system 800, the fuel pellet is also combusted in the combustion furnace 29 connected to the boiler 22, in addition to the combustion of the fuel pellet in the boiler 22, in the above-described waste treatment system 300 (see FIG. 3). The waste treatment system 700 is in a form which is preferred in a case in which, for example, the waste treatment system 700 is newly installed with respect to an already-existing thermal power plant or the like including the boiler 22 for combusting a fossil fuel.

The combustion furnace 29 is constituted by, for example, the fluidized-bed furnace, obtaining a combustion exhaust gas by complete combustion of the fuel pellet in the combustion furnace 29. Then, using the above-described combustion gas, steam is generated by a heat recovery steam generator 30. That is, in the heat recovery steam generator 30, steam is generated by using the combustion energy in the combustion furnace 29 constituted by the fluidized-bed furnace for combusting the fuel pellet (fuel). Thus, with the fluidized-bed furnace, it is possible to combust the fuel rapidly while suppressing the variation in combustion. Thus, it is possible to generate steam rapidly while suppressing a variation in generation amount.

The generated steam is supplied to the steam turbine 23. On the other hand, the combustion exhaust gas that has generated the steam in the heat recovery steam generator 30 is supplied to the above-described drying device 12. Then, in the drying device 12, using the combustion exhaust gas generated by combustion of the fuel pellet, the solid reactant obtained in the solid-liquid separation device 11 is dried.

According to the waste treatment system 800, it is possible to increase the amount of the steam to be supplied to the steam turbine 23. Thus, it is possible to enhance power generation efficiency. Moreover, it is possible to dry the solid reactant by using the combustion exhaust gas generated in the combustion furnace 29.

Figure 9:
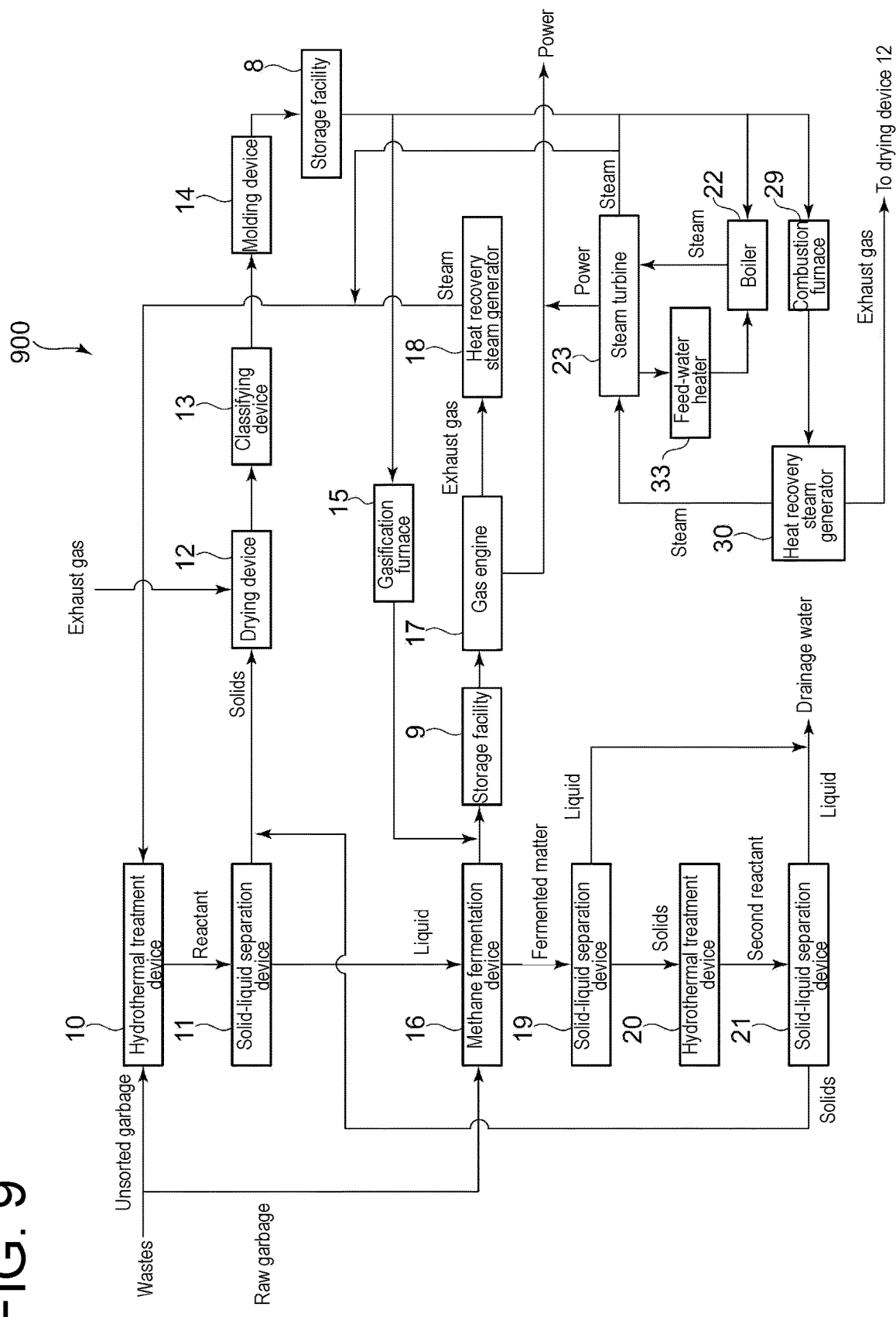
FIG. 9 is a system diagram of a waste treatment system according to the ninth embodiment of the present invention.

FIG. 9 is a system diagram of a waste treatment system 900 according to the eighth embodiment of the present invention. The waste treatment system 900 includes the combustion furnace 29 which is the fluidized-bed furnace for combusting the fuel, and a feed-water heater 33 for heating water to be supplied to the boiler 22 (steam generation device). Then, the feed-water heater 33 is configured to heat water by using the combustion energy generated in the combustion furnace 29 which is the fluidized-bed furnace. Therefore, in the waste treatment system 900 shown in FIG. 9, the combustion exhaust gas discharged from the heat recovery steam generator 30 is supplied to the feed-water heater 33 for heating water returning from the steam turbine 23 to the boiler 22, in addition to being supplied to the drying device 12, in the above-described waste treatment system 800 (see FIG. 8).

According to the waste treatment system 900, it is possible to supply the water, whose temperature is increased by the feed-water heater 33, to the boiler 22. Thus, it is possible to increase the steam generation amount and to enhance power generation efficiency. Moreover, with the fluidized-bed furnace, it is possible to combust the fuel rapidly while suppressing the variation in combustion. Thus, it is possible to generate steam rapidly while suppressing the variation in generation amount.

Figure 10:
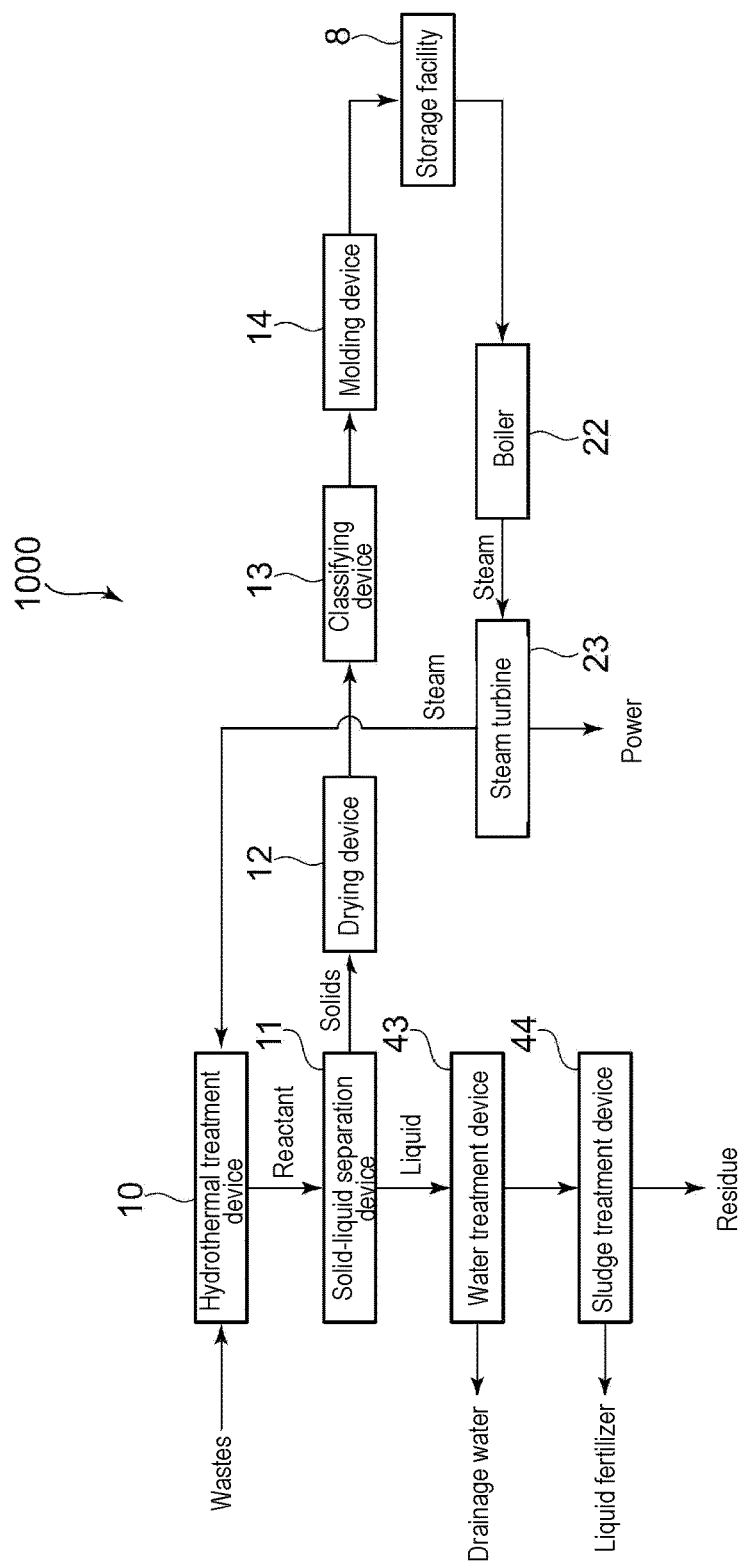
FIG. 10 is a system diagram of a waste treatment system according to the tenth embodiment of the present invention.

FIG. 10 is a system diagram of a waste treatment system 1000 according to the tenth embodiment of the present invention. Unlike the above-described waste treatment systems 100 to 900, the waste treatment system 1000 does not include the methane fermentation device 16. Thus, the liquid separated by the solid-liquid separation device 11 is supplied to a water treatment device 43. In the water treatment device 43, salts and the like in the supplied liquid are flocculated by a flocculating agent (not shown). Consequently, the salts and the like in the liquid are removed and drained to the outside. Moreover, the flocculating agent is dried in a sludge treatment device 44. Then, a liquid fertilizer (liquid manure) is obtained from some of dry matters, and a residue is obtained as a remnant. The residue undergoes incineration treatment, as needed.

According to the waste treatment system 1000, it is possible to produce the liquid fertilizer (compost) from the wastes. Moreover, since the fuel pellet, which is derived from the reactant after the hydrothermal treatment of the wastes and has a low salt content, is incinerated in the boiler 22, it is possible to suppress corrosion of the boiler 22.

Figure 11:
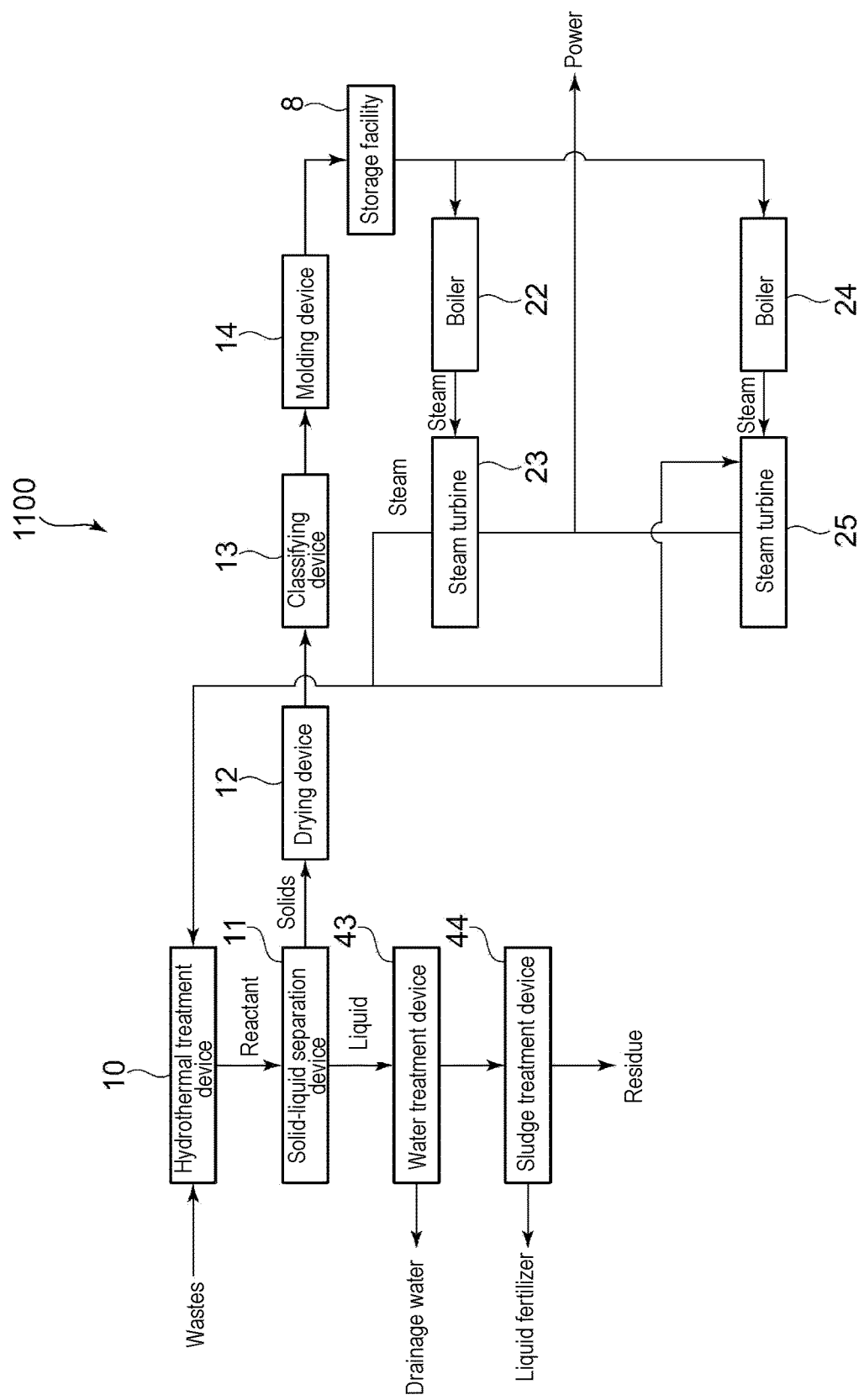
FIG. 11 is a system diagram of a waste treatment system according to the eleventh embodiment of the present invention.

FIG. 11 is a system diagram of a waste treatment system 1100 according to the eleventh embodiment of the present invention. As with the above-described waste treatment system 1000 (see FIG. 10), the waste treatment system 1100 does not include the methane fermentation device 16. Then, as with the above-described waste treatment system 400 (see FIG. 4), the waste treatment system 1100 includes the boilers 22, 24 and the steam turbines 23, 25 (that is, two power generation devices). Therefore, for example, it is possible to generate power with the steam turbine 25 by generating water vapor in the boiler 24 as needed, while driving the steam turbine 23 with the water vapor generated in the boiler 22.

According to the waste treatment system 1100, it is possible to optionally change the number of power generation devices (the boilers and the steam turbines) used, in accordance with the power demand. Thus, it is possible to flexibly change the power generation amount in accordance with the power demand, and to stably supply power.

Figure 12:
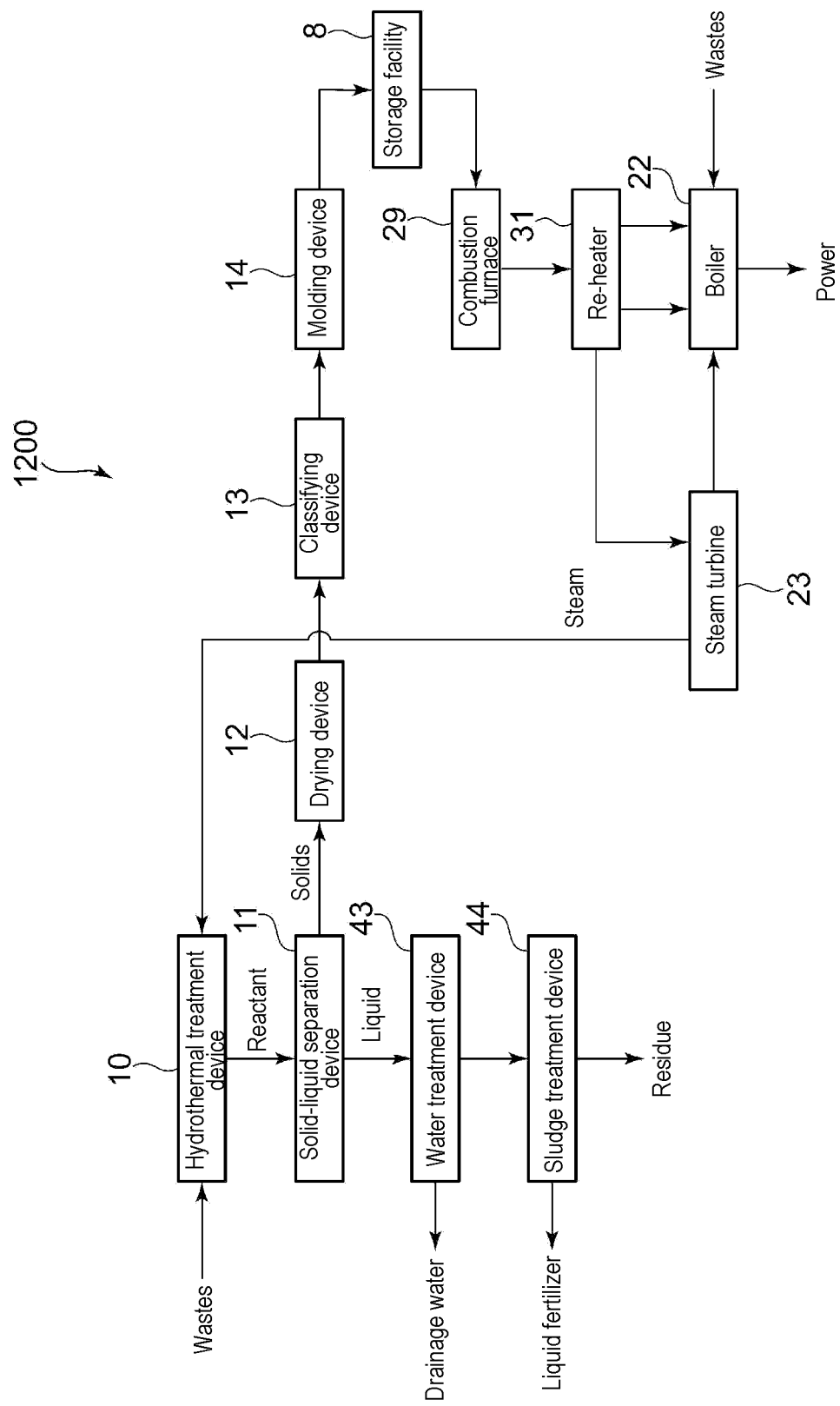
FIG. 12 is a system diagram of a waste treatment system according to the twelfth embodiment of the present invention.

FIG. 12 is a system diagram of a waste treatment system 1200 according to the twelfth embodiment of the present invention. As with the above-described waste treatment system 1000 (see FIG. 10), as with the above-described waste treatment system 1000 (see FIG. 10), the waste treatment system 1200 does not include the methane fermentation device 16. Then, as with the above-described waste treatment system 600 (see FIG. 6), the waste treatment system 1100 includes the combustion furnace 29 and the re-heater 31 Moreover, as with the above-described waste treatment system 600, the wastes of high water content is combusted in the boiler 22.

According to the waste treatment system 1200, it is possible to produce superheated steam and to enhance power generation efficiency, even for the boiler 22 for combusting the wastes of high water content.

Figure 13:
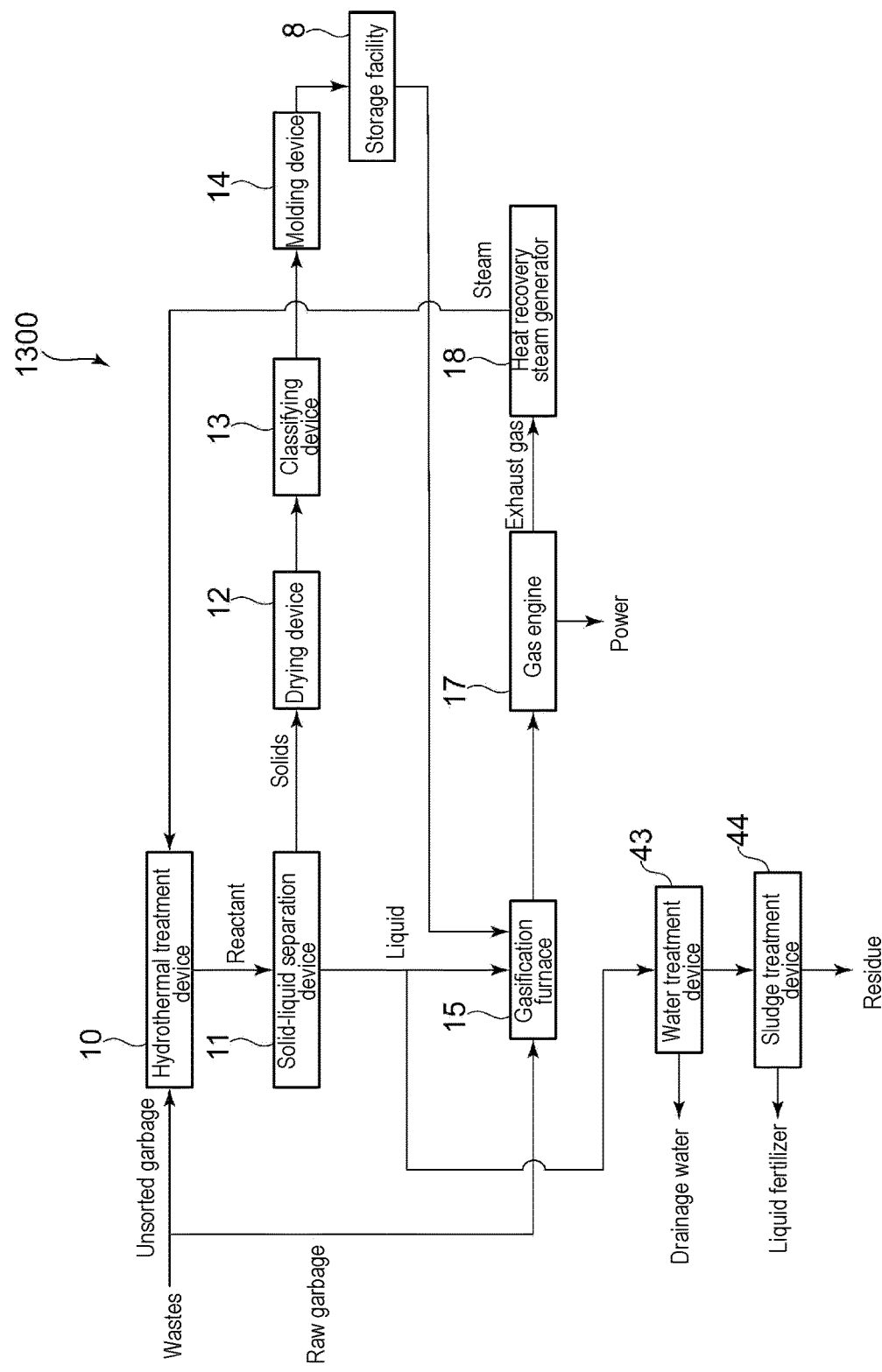
FIG. 13 is a system diagram of a waste treatment system according to the thirteenth embodiment of the present invention.

FIG. 13 is a system diagram of a waste treatment system 1300 according to the thirteenth embodiment of the present invention. As with the above-described waste treatment system 1000 (see FIG. 10), the waste treatment system 1300 does not include the methane fermentation device 16. Then, as with the above-described waste treatment system 100 (see FIG. 1), the waste treatment system 1300 includes the gasification furnace 15, the gas engine 17, and the heat recovery steam generator 18

In the waste treatment system 1300, the liquid separated in the solid-liquid separation device 11 is combusted together with the fuel pellet in, for example, the gasification furnace 15 constituted by the fluidized-bed furnace, in addition to being treated in the above-described water treatment device 43. Thus, according to the waste treatment system 1300, it is possible to reduce a water treatment amount in the water treatment device 43, and to reduce the amount of residues generated in the sludge treatment device 44 in the latter stage.

Figure 14:
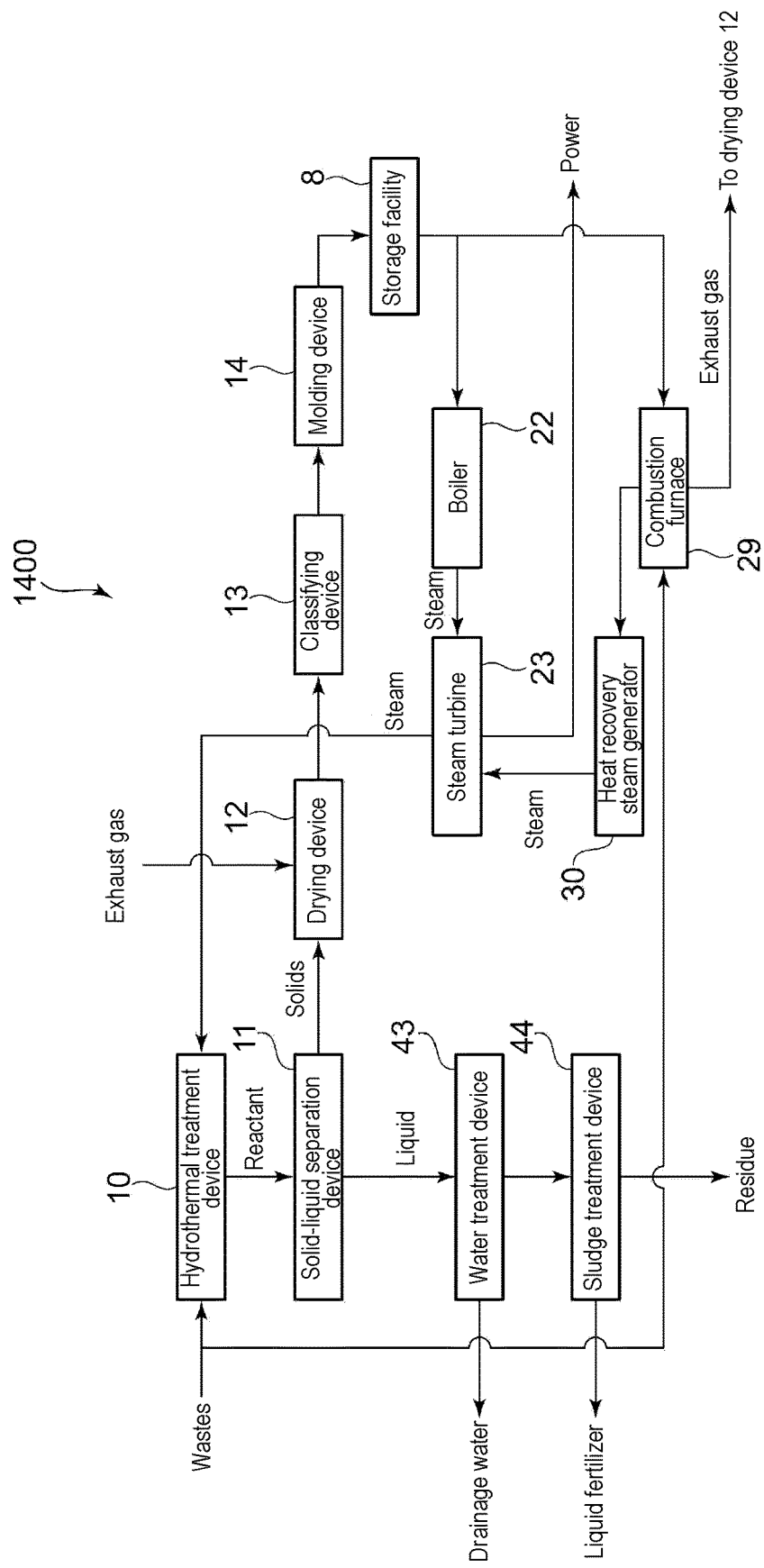
FIG. 14 is a system diagram of a waste treatment system according to the fourteenth embodiment of the present invention.

FIG. 14 is a system diagram of a waste treatment system 1400 according to the fourteenth embodiment of the present invention. As with the above-described waste treatment system 1000 (see FIG. 10), the waste treatment system 1400 does not include the methane fermentation device 16. Then, as with the above-described waste treatment system 800 (see FIG. 8), the waste treatment system 1400 includes the combustion furnace 29 and the heat recovery steam generator 30. In the waste treatment system 1400, the wastes are combusted, in addition to the fuel pellet (may be a dry matter before being classified), in the combustion furnace 29.

According to the waste treatment system 1400, it is possible to increase the amount of the steam to be supplied to the steam turbine 23. In particular, since the wastes are combusted in the combustion furnace 29, the heating value is further increased, compared to the above-described waste treatment system 800. Thus, it is possible to further increase the amount of the steam to be supplied to the steam turbine 23, and to further enhance power generation efficiency.

Figure 15:
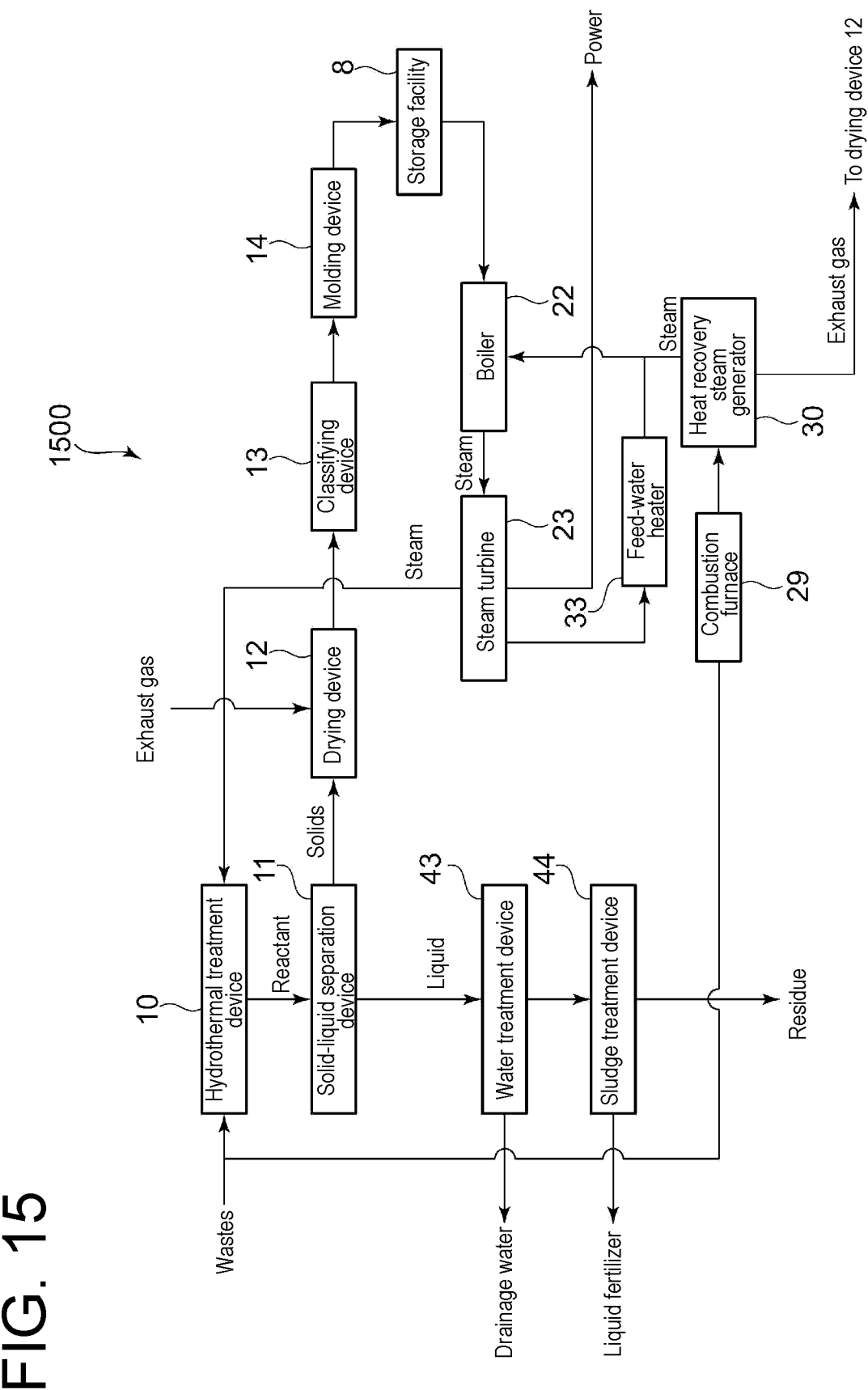
FIG. 15 is a system diagram of a waste treatment system according to the fifteenth embodiment of the present invention.

FIG. 15 is a system diagram of a waste treatment system 1500 according to the fifteenth embodiment of the present invention. As with the above-described waste treatment system 1000 (see FIG. 10), the waste treatment system 1500 does not include the methane fermentation device 16. Then, as with the above-described waste treatment system 900 (see FIG. 9), the waste treatment system 1500 includes the combustion furnace 29, the heat recovery steam generator 30, and the feed-water heater 33. Moreover, in the waste treatment system 1500, the wastes are combusted, in addition to the fuel pellet (may be the dry matter before being classified), in the combustion furnace 29.

According to the waste treatment system 1500, it is possible to supply the water, whose temperature is increased by the feed-water heater 33, to the boiler 22. Thus, it is possible to increase the steam generation amount and to enhance power generation efficiency. In particular, since the wastes are combusted in the combustion furnace 29, the heating value is further increased, compared to the above-described waste treatment system 800. Thus, it is possible to further increase the amount of the steam to be supplied to the steam turbine 23, and to further enhance power generation efficiency.

Figure 16:
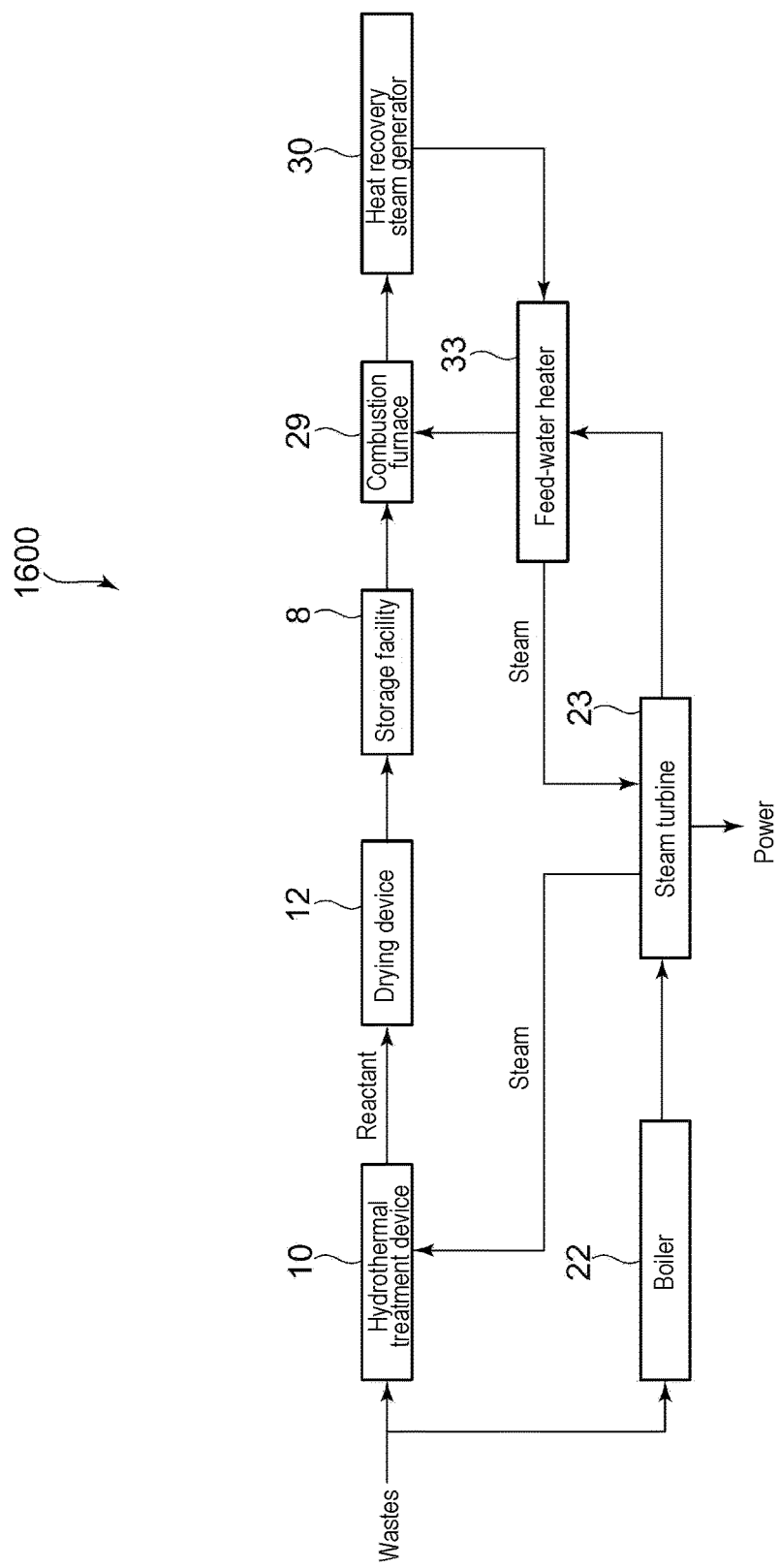
FIG. 16 is a system diagram of a waste treatment system according to the sixteenth embodiment of the present invention.

FIG. 16 is a system diagram of a waste treatment system 1600 according to the sixteenth embodiment of the present invention. As with the above-described waste treatment system 1000 (see FIG. 10), the waste treatment system 1600 does not include the methane fermentation device 16. Then, the reactant obtained in the hydrothermal treatment device 10 is dried by the drying device 12 to be the dry matter, and then the dry matter is combusted in the combustion furnace 29. However, the fuel pellet is produced from the dry matter, and the produced fuel pellet may be combusted in the combustion furnace 29. Steam is generated in the heat recovery steam generator 30 from the combustion energy generated in the combustion furnace 29. The generated steam is supplied to the feed-water heater 33, and the supplied steam heats the steam used in the steam turbine 23. Then, the steam, which is supplied from the heat recovery steam generator 30 and used to heat the steam, is supplied to the combustion furnace 29.

Moreover, the waste treatment system 1600 includes the boiler 22 for combusting the wastes, the steam turbine 23, and the generator body part (not shown) connected to the steam turbine 23. These are provided for the facility such as the already-existing thermal power plant or a garbage incineration plant (not shown). Then, the steam generated in the heat recovery steam generator 30 described above is supplied to the steam turbine 23. Then, the water (low-temperature steam) that has been used in the steam turbine 23 is heated in the feed-water heater 33 and is used in the steam turbine 23 again. Therefore, the generator body part connected to the steam turbine 23 generates power by using both of the steam generated in the boiler 22 and the steam generated in the heat recovery steam generator 30.

According to the waste treatment system 1600, it is possible to supply steam to the already-existing facility, for example. Thus, using the wastes, it is possible to increase the power generation amount in the already-existing facility.

Figure 17:
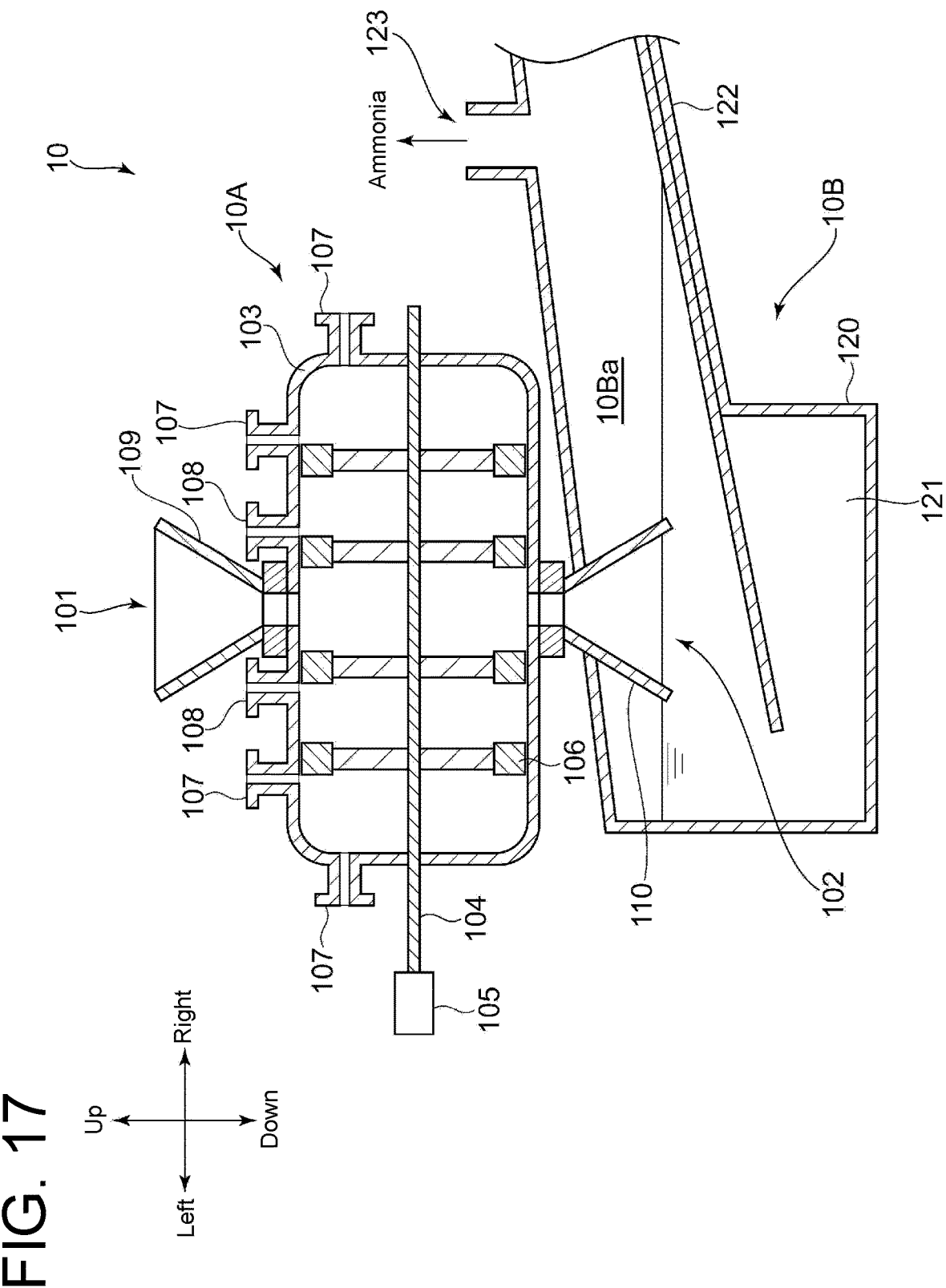
FIG. 17 is a cross-sectional view of a hydrothermal treatment device according to the seventeenth embodiment of the present invention.

FIG. 17 is a cross-sectional view of the hydrothermal treatment device 10 according to the seventeenth embodiment of the present invention. The hydrothermal treatment device 10 shown in FIG. 17 can be used in the above-described waste treatment systems 100 to 1600. The hydrothermal treatment device 10 includes a body part 10A for performing the hydrothermal treatment, and a bucket 10B for forming an interior space 10Ba communicating with the body part 10A via a discharge port 102 (reactant discharge port). The bucket 10B is provided to send a reactant discharged from the body part 10A to the solid-liquid separation device 11.

The body part 10A includes a slot 101 where the wastes are to be loaded, the discharge port 102 for discharging the reactant that has undergone the hydrothermal treatment, a housing 103 internally having a space where the hydrothermal treatment is to be performed and configured to be able to make the interior space airtight, a rotational shaft 104 with stirring blades 106 for stirring the wastes, and a motor 105 for rotating the rotational shaft 104. Moreover, the housing 103 includes steam supply ports 107 for injecting steam into the housing 103, and steam discharge ports 108 for discharging the steam from the inside of the housing 103. Furthermore, the above-described slot 101 is provided with a hopper 109, and the above-described discharge port 102 is also provided with a hopper 110.

The bucket 10B includes a water storage part 120 configured to have the interior thereof airtight and to store water 121, a conveyor 122 arranged to be immersed in the water 121 of the water storage part 120, and a gas extraction port 123 for extracting the gas entering into the bucket 10B through the discharge port 102. Then, the gas extraction port 123 of the bucket 10B is connected to a discharge pipe (not shown) for discharging the gas existing in the interior space 10Ba to the outside of the interior space 10Ba. The discharge pipe is connected to, for example, an exhaust gas treatment device (not shown).

With the hydrothermal treatment in the body part 10A, for example, ammonia or the like originating from nitrogen in the wastes can be generated inside the body part 10A. Thus, the gas such as ammonia entering the interior space 10Ba through the discharge port 102 is extracted to the outside of the interior space 10Ba through the gas extraction port 123.

Then, the gas such as ammonia undergoes the exhaust gas treatment in the exhaust gas treatment device (not shown) or the like, for example. Thus, it is possible to suppress discharge of the gas (such as ammonia or the like) exhausted to the bucket 10B to the atmosphere, when the reactant is extracted from the body part 10A.

Moreover, in the bucket 10B, the discharge port 102 of the body part 10A is arranged below a water surface of the water 121. Moreover, the conveyor 122 is connected to the solid-liquid separation device 11 which is not shown in FIG. 17. Therefore, the reactant obtained by the hydrothermal treatment in the body part 10A is conveyed to the solid-liquid separation device 11 by the conveyor 122.

Figure 18:
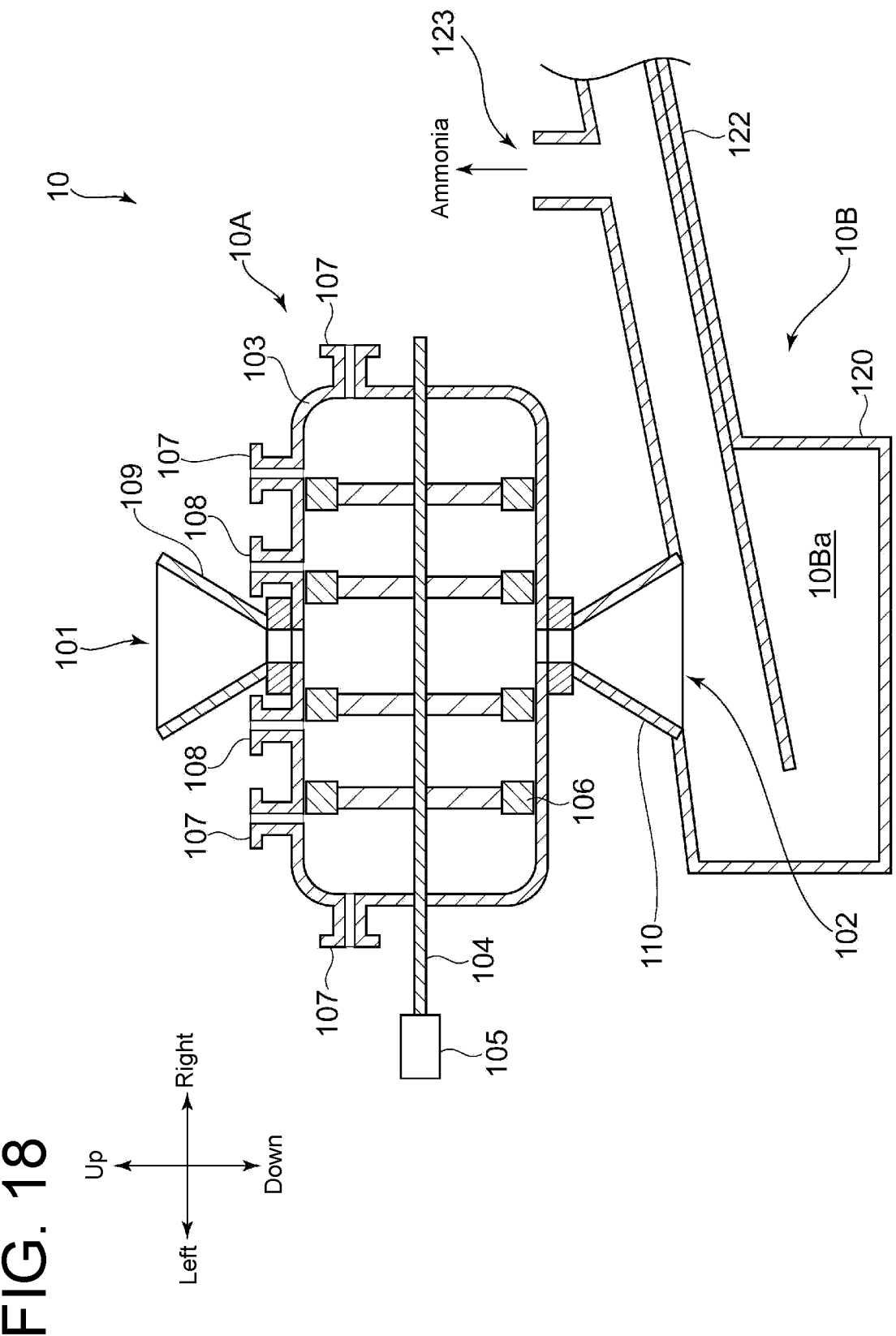
FIG. 18 is a cross-sectional view of the hydrothermal treatment device according to the eighteenth embodiment of the present invention.

FIG. 18 is a cross-sectional view of the hydrothermal treatment device 10 according to the eighteenth embodiment of the present invention. The hydrothermal treatment device 10 shown in FIG. 18 is in a form where the water 121 is not accommodated in the above-described hydrothermal treatment device 10 shown in FIG. 17. Even with such a hydrothermal treatment device 10 without accommodating the water 121, it is possible to obtain the reactant by the hydrothermal treatment.

As has been described with reference to, for example, the above-described waste treatment system 100 (see FIG. 1), the fuel pellet, which is obtained by drying and molding the reactant obtained in the hydrothermal treatment device 10 (may be the dry matter before being molded), is combusted in the gasification furnace 15 and the like. Thus, in order to perform combustion stably, the water content of the fuel pellet is preferably about the same, regardless of the period of the fuel pellet. Thus, it is possible to suppress a significant change in heating value owing to an extreme difference in water content, when the fuel pellet is combusted in the gasification furnace 15.

However, the water content of the wastes cannot be controlled in advance, and the water content varies according to a period, season, site, and the like of collection. Moreover, in general, the wastes are temporarily put into, for example, a pit or the like, and the wastes are carried from the pit to the hydrothermal treatment device 10 by a crane or the like. Both of the pit and the crane are not shown. Then, the water content of the wastes carried to the hydrothermal treatment device 10 varies according to a gathered place in the pit by the crane or the like.

Thus, in the waste treatment systems 100 to 1600, the water content of at least one of the wastes or the reactant before being dried is preferably adjusted to equalize the water content of the fuel pellet obtained after the drying. Thus, it is unnecessary to change dry conditions in the drying device 12 for each reactant, making it possible to stably obtain the dry matter.

In order to adjust the water content of at least one of the wastes or the reactant before being dried, first, the water content of the wastes is predicted. The water content of the wastes can be predicted as follows, for example. More specifically, for example, capturing an image from a side surface of the pit, where the wastes are stored, by a spectrum camera or the like, it is possible to predict the water content of the wastes in the pit. Moreover, for example, when the wastes are gathered from the pit by the crane or the like, it is possible to predict a water content of the gathered wastes, based on a volume of the gathered wastes and a dry weight of organic wastes predicted from the volume.

Then, based on the predicted amount of the wastes, the water amount is adjusted in the hydrothermal treatment device 10 to equalize the water content in the solids to be supplied to the drying device 12 (more specifically, the reactant to be supplied to the solid-liquid separation device 11). More specifically, for example, if the water content of the wastes is low, for example, water may be input into the pit, water may be sprayed on the conveyor for conveying the wastes from the pit to the slot 101, or water may be input together when the wastes are loaded to the slot 101.

Furthermore, for example, water may directly be input into the body part 10A. In this case, for example, water for cleaning a packing of a ball valve (not shown) provided for the body part 10A to seal the slot 101 may be input into the body part 10A through the slot 101. Thus, it is possible to adjust moisture, as well as to clean the packing and to make the interior of the body part 10A more airtight with the ball valve.

Moreover, moisture may be adjusted in the bucket 10B, with respect to the reactant discharged from the discharge port 102. In particular, adjusting moisture in the bucket 10B, fluidity of the reactant is increased, making it possible to easily carry the reactant to the solid-liquid separation device 11.

The hydrothermal treatment device 10 shown in each of FIG. 18 and FIG. 17 described above is a batch hydrothermal treatment device. The hydrothermal treatment device includes a slot of about, for example, 400 to 600 mm where even a large waste can directly be loaded. For example, using the batch hydrothermal treatment device 10, it is possible to load the wastes to the hydrothermal treatment device 10 directly from the vehicle (not shown) for collecting the wastes, and to achieve pitless of the waste treatment systems 100 to 1600.

Figure 19:
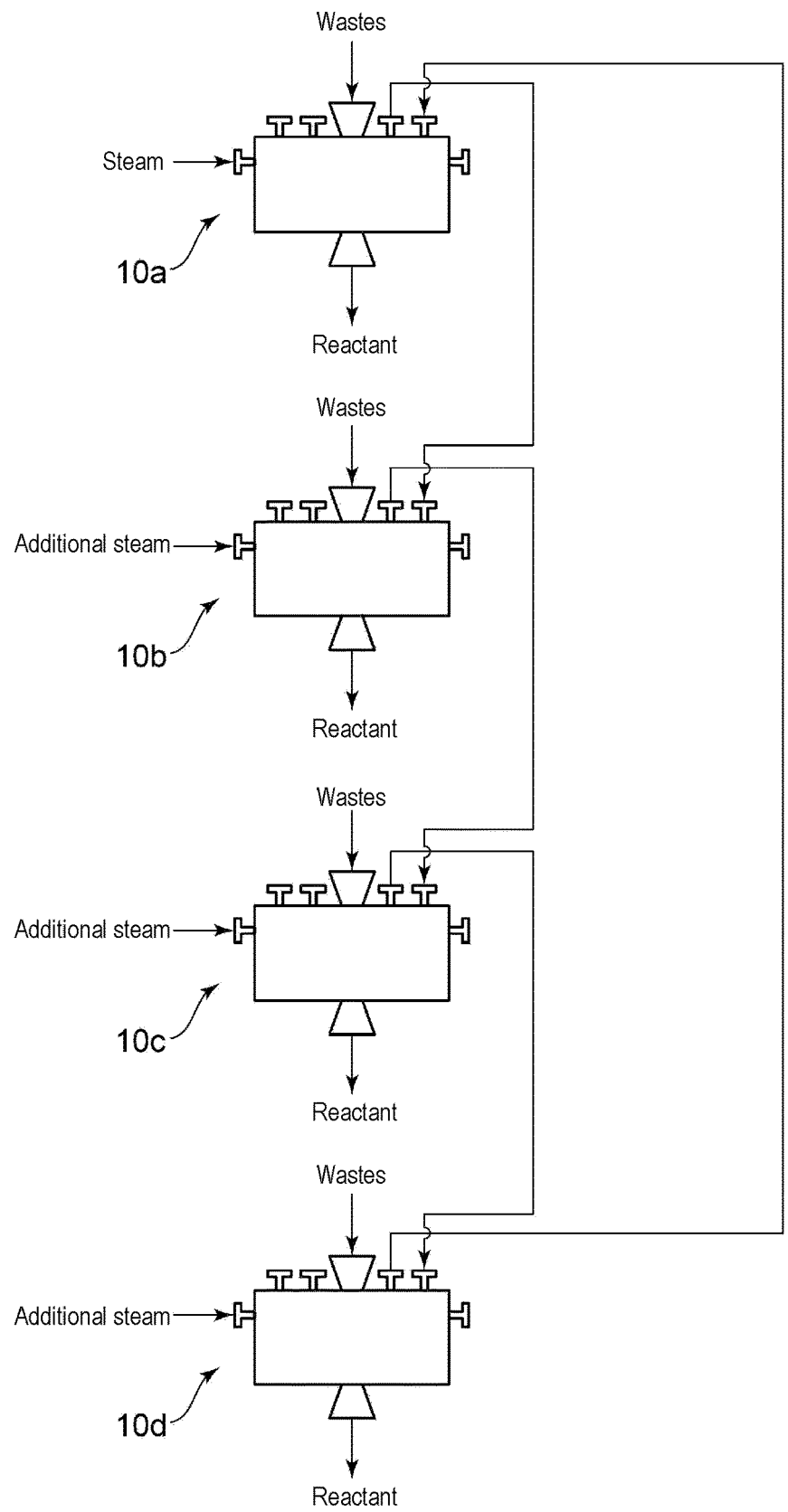
FIG. 19 is a view showing a flow of steam when a plurality of unit hydrothermal treatment devices are used in combination.

FIG. 19 is a view showing a flow of steam when a plurality of unit hydrothermal treatment devices 10a to 10d are used in combination. As shown in FIG. 19, the hydrothermal treatment device 10 includes the first unit hydrothermal treatment device 10a, the second unit hydrothermal treatment device 10b, the third unit hydrothermal treatment device 10c, and the fourth unit hydrothermal treatment device 10d. However, there may be two or three hydrothermal treatment devices 10, or there may be not less than five hydrothermal treatment devices 10.

These hydrothermal treatment devices 10 are connected in series. More specifically, for example, the steam discharge port 108 (not shown in FIG. 19) of the first unit hydrothermal treatment device 10a (first unit hydrothermal treatment device) and the steam supply port 107 of the second unit hydrothermal treatment device 10b (second unit hydrothermal treatment device) are connected by a pipe (not shown). Thus, it is possible to use steam, which has been used in the first unit hydrothermal treatment device 10, in the second unit hydrothermal treatment device 10b. Thus, it is possible to reduce a usage of new steam.

For example, in the first unit hydrothermal treatment device 10a, a hydrothermal treatment is performed by loading the wastes and supplying steam. Then, after the hydrothermal treatment, the reactant is extracted from the first unit hydrothermal treatment device 10a and supplied to the solid-liquid separation device 11 in the latter stage. On the other hand, the steam used in the first unit hydrothermal treatment device 10a is extracted from the first unit hydrothermal treatment device 10a through the steam discharge port 108. Then, the extracted steam is supplied into the second unit hydrothermal treatment device 10b through the steam supply port 107 of the second unit hydrothermal treatment device 10b. At this time, if the amount of the supplied steam is less than the amount of steam needed for the hydrothermal treatment, steam is added as needed. Thus, in the second unit hydrothermal treatment device 10b, the hydrothermal treatment is performed by reusing the steam supplied from the first unit hydrothermal treatment device 10a. Likewise, also in the third unit hydrothermal treatment device 10c and the fourth unit hydrothermal treatment device 10d, the hydrothermal treatment is performed while reusing steam.

Figure 20:
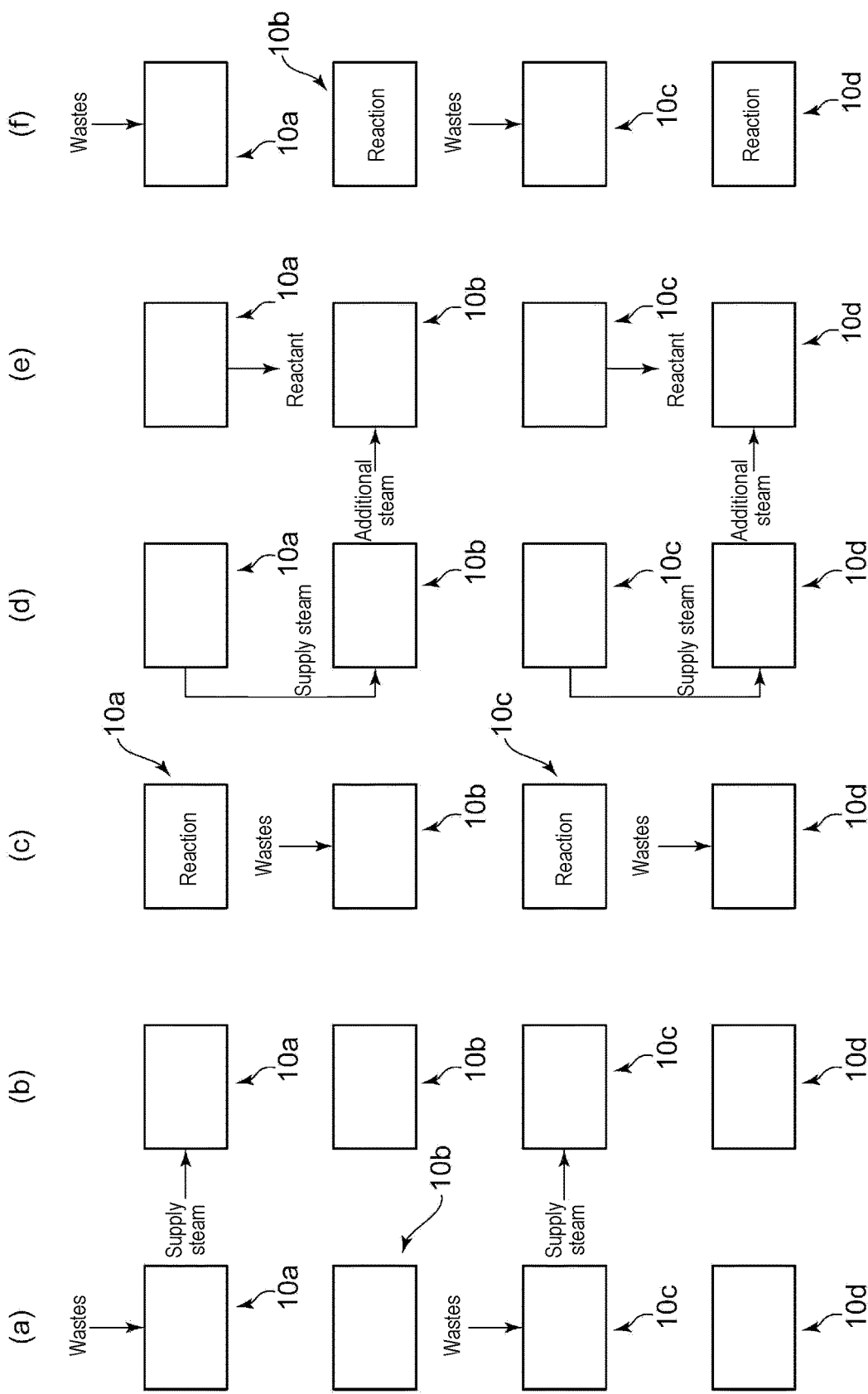
FIG. 20 are views for describing an action in each of the unit hydrothermal treatment devices when the plurality of unit hydrothermal treatment devices are used in combination.

FIG. 20 are views for describing an action in each of the unit hydrothermal treatment device 10 when the plurality of unit hydrothermal treatment devices 10 are used in combination. In an example shown in FIG. 20, as shown in FIG. 19 above, the hydrothermal treatment device 10 is constituted by the four hydrothermal treatment devices 10 (the first unit hydrothermal treatment device 10a, the second unit hydrothermal treatment device 10b, the third unit hydrothermal treatment device 10c, and the fourth unit hydrothermal treatment device 10d) used in combination. FIG. 20 shows a state in which the hydrothermal treatment device 10 is started.

First, of the four hydrothermal treatment devices 10, wastes are loaded to the first unit hydrothermal treatment device 10a and the third unit hydrothermal treatment device 10c, respectively ((a) of FIG. 20). Then, after the wastes are loaded, steams are supplied to the first unit hydrothermal treatment device 10a and the third unit hydrothermal treatment device 10c, respectively ((b) of FIG. 20). Consequently, the hydrothermal treatments of the wastes are performed in the first unit hydrothermal treatment device 10a and the third unit hydrothermal treatment device 10c, respectively.

In each of the second unit hydrothermal treatment device 10b and the fourth unit hydrothermal treatment device 10d, any particular operation is not performed at times shown in (a) of FIG. 20 and (b) of FIG. 20. However, wastes are also loaded to the second unit hydrothermal treatment device 10b and the fourth unit hydrothermal treatment device 10d, respectively, when the hydrothermal treatments are started in the first unit hydrothermal treatment device 10a and the third unit hydrothermal treatment device 10c, respectively, that is, at a time shown in (c) of FIG. 20.

On the other hand, when the hydrothermal treatments are ended in the first unit hydrothermal treatment device 10a and the third unit hydrothermal treatment device 10c, respectively, the steams used in the first unit hydrothermal treatment device 10a and the third hydrothermal treatment device 10c are supplied to the second unit hydrothermal treatment device 10b and the fourth unit hydrothermal treatment device 10d, respectively ((d) of FIG. 20). Then, reactants are extracted from housings (not shown) of the first unit hydrothermal treatment device 10a and the third unit hydrothermal treatment device 10c, respectively ((e) of FIG. 20).

Along with this, steams lost due to leakage or the like when the steams are supplied from the first unit hydrothermal treatment device 10a and the third unit hydrothermal treatment device 10c, that is, a shortage of the steams are supplied, as additional steams, to the second unit hydrothermal treatment device 10b and the fourth unit hydrothermal treatment device 10d, respectively ((e) of FIG. 20). Then, hydrothermal treatments are started in the second unit hydrothermal treatment device 10b and the fourth unit hydrothermal treatment device 10d, respectively ((f) of FIG. 20). On the other hand, new wastes are loaded to the first unit hydrothermal treatment device 10a and the third unit hydrothermal treatment device 10c where the reactants are extracted, becoming empty inside, respectively ((f) of FIG. 20).

Figure 21:
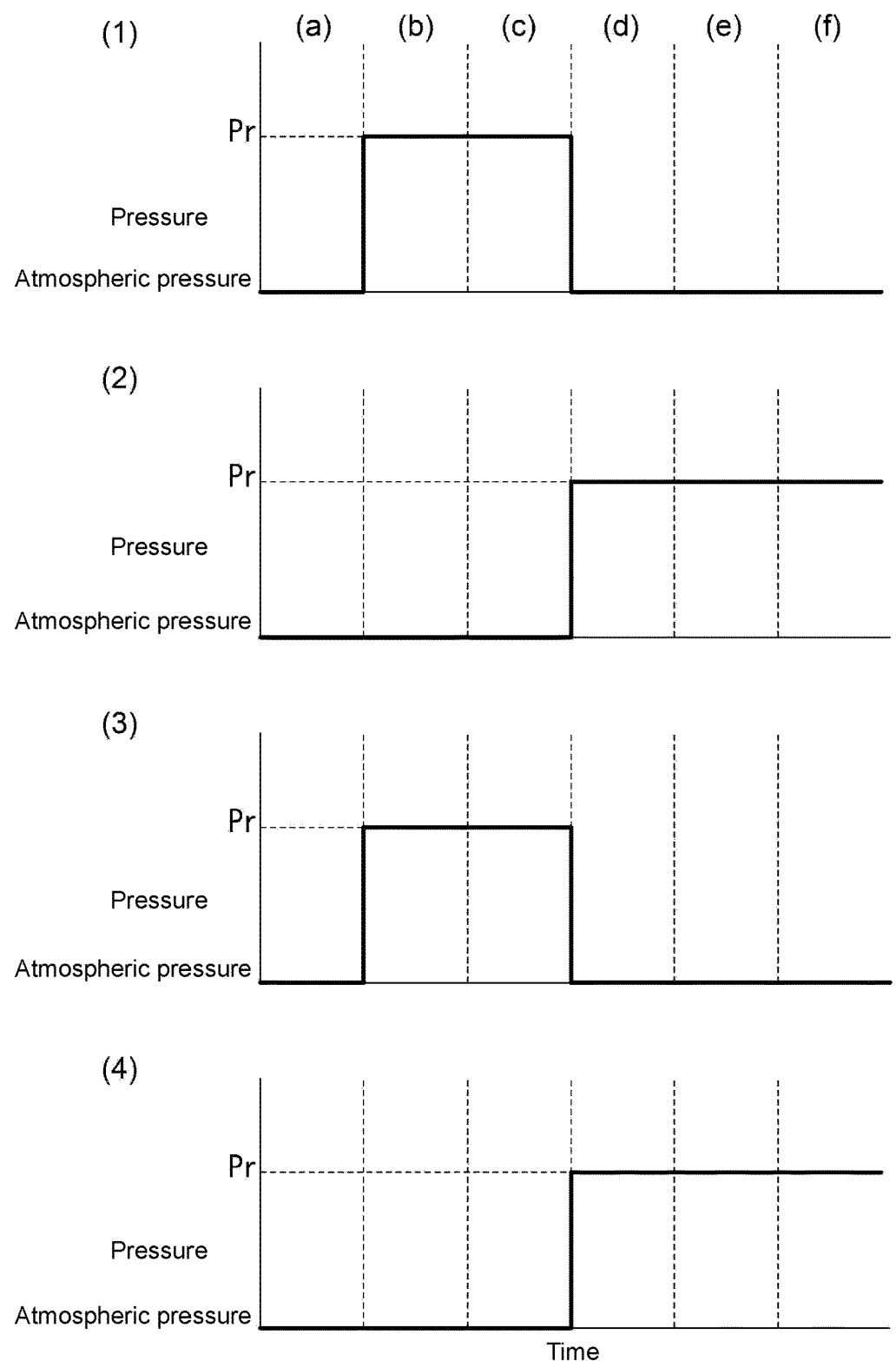
FIG. 21 are time charts showing an inner pressure change in each of the unit hydrothermal treatment devices shown in FIG. 20.

FIG. 21 are time charts showing an inner pressure change in each of the unit hydrothermal treatment devices 10 shown in FIG. 20. (a) to (f) shown in FIG. 21 correspond to (a) to (f) shown in FIG. 20 above, respectively. As described above, the first unit hydrothermal treatment device 10a and the third unit hydrothermal treatment device 10c are driven at the same timing. Therefore, the inner pressure of the first unit hydrothermal treatment device 10a and the inner pressure of the third unit hydrothermal treatment device 10c also change at the same timing. On the other hand, the second unit hydrothermal treatment device 10b and the fourth unit hydrothermal treatment device 10d are driven at the same timing. Therefore, the inner pressure of the second unit hydrothermal treatment device 10b and the inner pressure of the fourth unit hydrothermal treatment device 10d also change at the same timing.

As shown in (a) of FIG. 21, the inner pressure of each of the first unit hydrothermal treatment device 10a and the third unit hydrothermal treatment device 10c when the wastes are loaded is an atmospheric pressure. Moreover, the inner pressure of each of the first unit hydrothermal treatment device 10a and the third unit hydrothermal treatment device 10c, which have not been driven yet at this time, is also the atmospheric pressure. Then, injecting steam to each of the first unit hydrothermal treatment device 10a and the third unit hydrothermal treatment device 10c where the wastes are loaded, the inner pressure of each of the first unit hydrothermal treatment device 10a and the third unit hydrothermal treatment device 10c is increased to a pressure $P_r$, and the hydrothermal treatment proceeds at the pressure $P_r$ ((b) and (c) of FIG. 21). The pressure $P_r$ is a pressure capable of causing the hydrothermal treatment.

On the other hand, in each of the second unit hydrothermal treatment device 10b and the forth unit hydrothermal treatment device 10d, the inner pressure thereof is increased to $P_r$ ((d) of FIG. 21) by the injection of the steam from each of the first unit hydrothermal treatment device 10a and the third unit hydrothermal treatment device 10c, after the wastes are loaded ((c) of FIG. 20). However, as described above, not all the steams that have been used in the first unit hydrothermal treatment device 10a and the third unit hydrothermal treatment device 10c, respectively, are supplied, due to, for example, leakage or the like, when the steams are supplied from the first unit hydrothermal treatment device 10a and the third unit hydrothermal treatment device 10c to the second unit hydrothermal treatment device 10b and the fourth unit hydrothermal treatment device 10d, respectively.

Thus, additional steam is injected to each of the second unit hydrothermal treatment device 10b and the fourth unit hydrothermal treatment device 10d, until the amount used for the hydrothermal treatment is obtained ((d) of FIG. 21). After the steams are supplied, the reactants are discharged from the first unit hydrothermal treatment device 10a and the third unit hydrothermal treatment device 10c, respectively ((e) of FIG. 20). Then, after the internal temperature of each of the first unit hydrothermal treatment device 10a and the third unit hydrothermal treatment device 10c is sufficiently decreased, the slot 101 is opened so that new wastes are loaded ((f) of FIG. 20). In particular, since the slot 101 is opened after the internal temperature of each of the first unit hydrothermal treatment device 10a and the third unit hydrothermal treatment device 10c is sufficiently decreased, the interior thereof has a negative pressure, suppressing release of an internal gas (for example, ammonia) to the outside through the slot 101. On the other hand, the hydrothermal treatments of the wastes proceed in the second unit hydrothermal treatment device 10b and the fourth unit hydrothermal treatment device 10d, respectively ((f) of FIG. 20).

Repeating the drive described above with reference to FIGS. 20 and 21, the plurality of hydrothermal treatments in the plurality of hydrothermal treatment devices 10 proceed simultaneously. Thus, it is possible to increase the hydrothermal treatment amount of the wastes and to increase the generation amount of the reactants. As a result, it is possible to treat the wastes efficiently.

REFERENCE SIGNS LIST 1, 17 Gas engine (power generation device; first power generation device, second power generation device, third power generation device)
8, 9 Storage facility (first storage facility, second storage facility, third storage facility)
10, 20, 26 Hydrothermal treatment device (fuel production device, first hydrothermal treatment device, second hydrothermal treatment device, third hydrothermal treatment device)
10A Body part
10B Bucket
10Ba Interior space
10a First unit hydrothermal treatment device
10b Second unit hydrothermal treatment device
10c Third unit hydrothermal treatment device
10d Fourth unit hydrothermal treatment device
11, 19, 21, 27 Solid-liquid separation device (fuel production device)
12, 28 Drying device (fuel production device)
13 Classifying device (fuel production device)
14 Molding device (fuel production device)
15 Gasification furnace
16 Methane fermentation device
18, 30 Heat recovery steam generator (steam generation device)
22, 24 Boiler (steam generation device)
23, 25 Steam turbine (power generation device; first power generation device, second power generation device, third power generation device)
29 Combustion furnace
31 Re-heater
33 Feed-water heater
43 Water treatment device
44 Sludge treatment device
100, 200, 300, 400, 500, 600, 700, 800, 900, 1000, 1100, 1200, 1300, 1400, 1500, 1600 Waste treatment system
101 Slot
102 Discharge port
103 Housing
104 Rotational shaft
105 Motor
106 Stirring blade
107 Steam supply port
108 Steam discharge port
109, 110 Hopper
120 Water storage part
121 Water
122 Conveyor
123 Gas extraction port

The invention claimed is:

1. A waste treatment system for performing a hydrothermal treatment of wastes, the system comprising:
a hydrothermal treatment device for performing the hydrothermal treatment by bringing steam into contact with the wastes, the hydrothermal treatment device including a housing in which the hydrothermal treatment is performed, a slot through which the wastes are loaded into the housing, a steam supply port through which the steam is injected into the housing, and a reactant discharge port through which a reactant of the hydrothermal treatment is discharged from the housing;
a fuel production device for producing a solid fuel from solids of the reactant of the hydrothermal treatment;
a methane fermentation device for performing methane fermentation of a liquid of the reactant to generate a biogas;
a first storage facility for storing the solid fuel;
a second storage facility for storing the biogas; and
at least one steam generation device for generating the steam to be supplied to the hydrothermal treatment device,
wherein the steam generation device is configured to generate the steam by using the solid fuel stored in the first storage facility or a combustion energy generated by combustion of the biogas stored in the second storage facility, and the fuel production device includes a drying device for drying the solids of the reactant.

2. The waste treatment system according to claim 1, further comprising:
a gasification furnace for gasifying the solid fuel to generate a fuel gas; and
a third storage facility for storing the fuel gas generated in the gasification furnace.

3. A waste treatment system for performing a hydrothermal treatment of wastes, the system comprising:
a first hydrothermal treatment device for performing a first hydrothermal treatment by bringing steam into contact with the wastes, the first hydrothermal treatment device including a housing in which the first hydrothermal treatment is performed, a slot through which the wastes are loaded into the housing, a steam supply port through which the steam is injected into the housing, and a reactant discharge port through which a reactant of the first hydrothermal treatment is discharged from the housing;
a methane fermentation device for performing methane fermentation of a liquid of the reactant of the first hydrothermal treatment to generate a biogas;
a second hydrothermal treatment device for performing a second hydrothermal treatment by bringing steam into contact with solids in a fermented matter obtained in the methane fermentation device;
a first storage facility for storing a solid fuel produced from each of solids of the reactant of the first hydrothermal treatment and solids of a reactant of the second hydrothermal treatment;
a second storage facility for storing the biogas; and
at least one steam generation device for generating the steam to be supplied to the first and second hydrothermal treatment devices,
wherein the steam generation device is configured to generate the steam by using the solid fuel stored in the first storage facility or a combustion energy generated by combustion of the biogas stored in the second storage facility.

4. The waste treatment system according to claim 3, wherein the second hydrothermal treatment device is configured to dry the solids of the reactant obtained by the second hydrothermal treatment.

5. The waste treatment system according to claim 1, further comprising a power generation device for generating power by using the solid fuel or the combustion energy generated by combustion of the biogas.

6. The waste treatment system according to claim 5, wherein the power generation device includes a steam turbine and a generator body part connected to the steam turbine, and
wherein the steam turbine is configured to be driven by at least a part of the steam generated in the steam generation device.

7. The waste treatment system according to claim 5, wherein the power generation device includes a gas engine and a generator body part connected to the gas engine, and
wherein the steam generation device is configured to generate steam by exhaust heat of the gas engine.

8. The waste treatment system according to claim 6, further comprising:
a combustion furnace for combusting the solid fuel; and
a re-heater for superheating the steam by using a combustion energy generated in the combustion furnace.

9. The waste treatment system according to claim 5, wherein the power generation device includes a first power generation device and a second power generation device.

10. The waste treatment system according to claim 5, further comprising a fluidized-bed furnace for combusting the solid fuel, and
wherein the steam generation device is configured to generate steam by using a combustion energy generated in the fluidized-bed furnace.

11. The waste treatment system according to claim 5, further comprising:
a fluidized-bed furnace for combusting the solid fuel; and
a feed-water heater for heating water to be supplied to the steam generation device, and
wherein the feed-water heater is configured to heat the water by using a combustion energy generated in the fluidized-bed furnace.

12. A waste treatment system for performing a hydrothermal treatment of wastes, the system comprising:
a first hydrothermal treatment device for performing a first hydrothermal treatment by bringing steam into contact with the wastes, the first hydrothermal treatment device including a housing in which the first hydrothermal treatment is performed, a slot through which the wastes are loaded into the housing, a steam supply port through which the steam is injected into the housing, and a reactant discharge port through which a reactant of the first hydrothermal treatment is discharged from the housing;
a second hydrothermal treatment device for performing a second hydrothermal treatment of wastes containing a resin, or containing an oil and a fat;
a fuel production device for producing a solid fuel from each of solids of the reactant of the first hydrothermal treatment and solids of a reactant of the second hydrothermal treatment;
a first storage facility for storing the solid fuel; and
at least one steam generation device for generating the steam to be supplied to the first and second hydrothermal treatment devices,
wherein the steam generation device is configured to generate the steam by using a combustion energy generated by combustion of the solid fuel stored in the first storage facility, and the fuel production device includes a drying device for drying the solids of the reactants of the first and second hydrothermal treatments.

13. A waste treatment system for performing a hydrothermal treatment of wastes, the system comprising:
at least one hydrothermal treatment device for performing the hydrothermal treatment by bringing steam into contact with the wastes, the at least one hydrothermal treatment device including a housing in which the hydrothermal treatment is performed, a slot through which the wastes are loaded into the housing, a steam supply port through which the steam is injected into the housing, and a reactant discharge port through which a reactant of the hydrothermal treatment is discharged from the housing;
at least one storage facility for storing a fuel produced from the reactant of the hydrothermal treatment; and
at least one steam generation device for generating the steam to be supplied to the at least one hydrothermal treatment device,
wherein the at least one steam generation device is configured to generate the steam by using a combustion energy generated by combustion of the fuel stored in the at least one storage facility.

14. The waste treatment system according to claim 1, wherein the hydrothermal treatment device is a first hydrothermal treatment device and includes a steam discharge port,
wherein the waste treatment system further comprise a second hydrothermal treatment device having a steam supply port and a steam discharge port, and
wherein the steam discharge port of one of the first and second hydrothermal treatment devices and the steam supply port of the other of the first and second hydrothermal treatment devices are connected by a pipe.

15. The waste treatment system according to claim 1, wherein the hydrothermal treatment device includes a batch hydrothermal treatment device.

16. The waste treatment system according to claim 1, wherein the hydrothermal treatment device includes a bucket configured to send the reactant discharged from the reactant discharge port to a solid-liquid separation device, and wherein an interior of the bucket communicates with an interior of the housing via the reactant discharge port.

17. The waste treatment system according to claim 16, wherein the bucket of the hydrothermal treatment device includes:
a water storage part in which water is stored so as to define an interior space between a surface of the water in the water storage part and an uppermost surface of the interior of the bucket;
a conveyor arranged so as to be immersed in the water in the water storage part; and
a gas extraction port connected to a discharge pipe for discharging a gas existing in the interior space to an outside of the interior space, wherein the reactant discharge port of the hydrothermal treatment device is arranged at least partially below the surface of the water in the water storage part.

18. The waste treatment system according to claim 3, wherein the first hydrothermal treatment device includes a bucket configured to send the reactant discharged from the reactant discharge port to a solid-liquid separation device, and wherein an interior of the bucket communicates with an interior of the housing via the reactant discharge port.

19. The waste treatment system according to claim 18, wherein the bucket of the first hydrothermal treatment device includes:
- a water storage part in which water is stored so as to define an interior space between a surface of the water in the water storage part and an uppermost surface of the interior of the bucket;
- a conveyor arranged so as to be immersed in the water in the water storage part; and
- a gas extraction port connected to a discharge pipe for discharging a gas existing in the interior space to an outside of the interior space, wherein the reactant discharge port of the first hydrothermal treatment device is arranged at least partially below the surface of the water in the water storage part.

20. The waste treatment system according to claim 12, wherein the first hydrothermal treatment device includes a bucket configured to send the reactant discharged from the reactant discharge port to a solid-liquid separation device, and wherein an interior of the bucket communicates with an interior of the housing via the reactant discharge port.

21. The waste treatment system according to claim 20, wherein the bucket of the first hydrothermal treatment device includes:
- a water storage part in which water is stored so as to define an interior space between a surface of the water in the water storage part and an uppermost surface of the interior of the bucket;
- a conveyor arranged so as to be immersed in the water in the water storage part; and
- a gas extraction port connected to a discharge pipe for discharging a gas existing in the interior space to an outside of the interior space, wherein the reactant discharge port of the first hydrothermal treatment device is arranged at least partially below the surface of the water in the water storage part.

22. The waste treatment system according to claim 13, wherein the at least one hydrothermal treatment device includes a bucket configured to send the reactant discharged from the reactant discharge port to a solid-liquid separation device, and wherein an interior of the bucket communicates with an interior of the housing via the reactant discharge port.

23. The waste treatment system according to claim 22, wherein the bucket of the at least one hydrothermal treatment device includes:
- a water storage part in which water is stored so as to define an interior space between a surface of the water in the water storage part and an uppermost surface of the interior of the bucket;
- a conveyor arranged so as to be immersed in the water in the water storage part; and
- a gas extraction port connected to a discharge pipe for discharging a gas existing in the interior space to an outside of the interior space, wherein the reactant discharge port of the at least one hydrothermal treatment device is arranged at least partially below the surface of the water in the water storage part.

* * * * *